(12) United States Patent
Smith et al.

(10) Patent No.: US 9,250,183 B2
(45) Date of Patent: Feb. 2, 2016

(54) LUMINESCENT MATERIALS, ARTICLES INCORPORATING LUMINESCENT MATERIALS, AND METHODS FOR PERFORMING ARTICLE AUTHENTICATION

(71) Applicant: Honeywell International Inc., Morristown, NJ (US)

(72) Inventors: Karl J. Smith, Sparta, NJ (US); Howard A. Fraenkel, Lebanon, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 267 days.

(21) Appl. No.: 13/708,210

(22) Filed: Dec. 7, 2012

(65) Prior Publication Data

US 2013/0153789 A1    Jun. 20, 2013

Related U.S. Application Data

(60) Provisional application No. 61/577,543, filed on Dec. 19, 2011.

(51) Int. Cl.
*F21V 9/16* (2006.01)
*G01N 21/63* (2006.01)
(Continued)

(52) U.S. Cl.
CPC ............ *G01N 21/63* (2013.01); *G01N 21/6408* (2013.01); *G01N 21/6428* (2013.01); *G07D 7/0006* (2013.01); *G07D 7/122* (2013.01)

(58) Field of Classification Search
CPC .................................................. G01N 21/6428
USPC ........................................... 250/458.1, 459.1
See application file for complete search history.

(56) References Cited

U.S. PATENT DOCUMENTS 4,500,116 A    2/1985    Ferro et al.
6,402,986 B1    6/2002    Jones, II et al.
(Continued)

FOREIGN PATENT DOCUMENTS

JP    2011144244 A    7/2010
WO    2011041657 A1    4/2011

OTHER PUBLICATIONS

The International Search Report mailed Mar. 22, 2013 in International Application No. PCT/US2012/068911.
(Continued)

*Primary Examiner* — David Porta
*Assistant Examiner* — Meenakshi Sahu
(74) *Attorney, Agent, or Firm* — Ingrassia Fisher & Lorenz PC

(57) ABSTRACT

Embodiments of luminescent materials and articles include first and second particles of first and second inorganic host lattices. The first particles are capable of producing first emissions having one or more first emission peaks at one or more first wavelengths. The first emissions have a first decay half-life that is long enough for the first emissions to be perceptible to the human eye for a first time period that begins when appropriate excitation of the luminescent material is discontinued. The second particles are capable of producing second emissions having one or more second emission peaks at one or more second wavelengths. The second emissions have a second decay half-life that is longer than the first decay half-life by a decay time difference that is sufficient for the second emissions to be perceptible to the human eye for a second time period that begins after the first time period.

17 Claims, 7 Drawing Sheets

(51) Int. Cl.
*G01N 21/64* (2006.01)
*G07D 7/00* (2006.01)
*G07D 7/12* (2006.01)

(56) References Cited

U.S. PATENT DOCUMENTS

| | | | |
|---|---|---|---|
| 6,602,716 | B1 | 8/2003 | Klimant |
| 7,213,757 | B2 | 5/2007 | Jones et al. |
| 7,495,234 | B2 | 2/2009 | Roth |
| 2004/0169847 | A1 | 9/2004 | Dukler |
| 2005/0067489 | A1 | 3/2005 | Jones et al. |
| 2006/0164004 | A1* | 7/2006 | Rossner ................. 313/503 |
| 2006/0180792 | A1* | 8/2006 | Ricci et al. ............ 252/301.16 |
| 2007/0295116 | A1 | 12/2007 | Le Mercier et al. |
| 2010/0026991 | A1 | 2/2010 | Heer et al. |
| 2012/0217416 | A1* | 8/2012 | Decoux .................. 250/459.1 |
| 2013/0193346 | A1 | 8/2013 | Justel et al. |

OTHER PUBLICATIONS

European Patent Office, European Search Report for Application No. 12860811.4 dated Jun. 23, 2015.

* cited by examiner

LUMINESCENT MATERIALS, ARTICLES INCORPORATING LUMINESCENT MATERIALS, AND METHODS FOR PERFORMING ARTICLE AUTHENTICATION

PRIORITY CLAIMS

This application claims the benefit of U.S. Provisional Application No. 61/577,543, filed Dec. 19, 2011.

TECHNICAL FIELD

The present invention generally relates to radiation emitting compounds and methods and apparatus for their use as security materials.

BACKGROUND

Many luminescent materials are capable of producing detectable emissions (i.e., output radiation of relatively high spectral energy) in the infrared, visible, and/or ultraviolet portions of the electromagnetic spectrum upon excitation of the materials by appropriate external energy sources. When a luminescent material emits radiation, the emission occurs over a discrete span of time, which may be defined by a measurable decay rate expressed as a decay half-life (i.e., a time period for an emission to reach 50 percent of its peak intensity) or some other quantity. Materials typically described as "fluorophors" (or "fluorescent") exhibit very short emission decay rates, with half-lives in the micro-, nano- or pico-second range. Conversely, materials typically described as "phosphors" exhibit longer decay rates, with half-lives ranging from several milliseconds to minutes or more (e.g., up to many hours). When the wavelength of a sufficiently-intense emission is in the visible region of the electromagnetic spectrum and its decay half-life is long enough (e.g., greater than the temporal threshold for human perception), the emissions can be observed by the human eye as having a color and brightness (or intensity). Once the excitation has been discontinued, the emissive color decays as a diminishingly observable afterglow, which eventually dies out completely.

A typical luminescent phosphor compound includes at least a host material (e.g., a crystalline composition or crystal lattice), an emitting ion, and in some cases, a "sensitizing" ion (e.g., an ion that can absorb and transfer excitation energy to an emitting ion). The production of radiation by a phosphor compound is accomplished either by absorption of incident radiation (also referred to as "excitation energy") by an emitting ion and radiation of the energy by the emitting ion, or by absorption of incident radiation by either or both the host material and a sensitizing ion, followed by energy transfer from the host material/sensitizing ion to the emitting ion, and subsequent radiation of the transferred energy by the emitting ion.

The selected components of a phosphor compound may cause the compound to have particular emission properties, including specific wavelengths for its excitation energy, and specific spectral position(s) for its emissions. For a specific phosphor compound that produces observable emissions, the spectral position(s) of the higher spectral energy content (or luminescent output) in its emissions (i.e., its "spectral signature") may be used to uniquely identify the phosphor compound from other compounds. Primarily, the spectral signature is due to the particular emitting ion(s) included within the phosphor compound. However, spectral perturbations may be present due to the influence of the host material on the various emitting ions, typically through crystal field strength and splitting. This holds true for the temporal behavior of the emissions, as well.

The unique spectral properties of some phosphor compounds make them well suited for use in authenticating or identifying articles of particular value or importance (e.g., banknotes, passports, biological samples, and so on). Accordingly, luminescent phosphor compounds with known spectral signatures have been incorporated into various types of articles to enhance the ability to detect forgeries or counterfeit copies of such articles, or to identify and track the articles. For example, luminescent phosphor compounds have been incorporated into various types of articles in the form of additives, coatings, and printed or otherwise applied features that may be analyzed in the process of authenticating or tracking an article.

An article that includes a luminescent phosphor compound may be authenticated through human observation and/or using specially designed authentication equipment. More particularly, a manufacturer may incorporate a known phosphor compound (e.g., an "authenticating" phosphor compound) into its "authentic" articles. As mentioned previously, phosphor compounds having emission wavelengths in the visible portion of the electromagnetic spectrum with sufficiently long decay half-lives may be observable by the human eye. Such a phosphor compound may be excited using a stationary or portable excitation source that produces excitation energy that is absorbable by the phosphor compound. When the excitation source is removed, the phosphor compound emits light of a particular wavelength for a period of time (e.g., a few seconds). When the emitted light is of an expected color, the human observer may deem the article to be authentic. Conversely, when the phosphor compound emits light of an unexpected color or fails to emit light of a sufficient intensity, the human observer may consider the article to be unauthentic (e.g., a forged or counterfeited article).

Suitably-configured authentication equipment may be used to detect the presence of phosphor compounds having emission wavelengths in the ultraviolet, visible, and infrared portions of the electromagnetic spectrum. When used for authentication, the authentication equipment has knowledge (e.g., stored information and/or a variety of spectral filters) of the wavelengths of absorbable excitation energy and the spectral properties of emissions associated with an authenticating phosphor compound. When provided with a sample article for authentication, the authentication equipment exposes the article to excitation energy having wavelengths that correspond with the known wavelengths of absorption features of the luminescent phosphor compound that lead directly or indirectly to the desired emissions. The authentication equipment senses and characterizes the spectral parameters for any emissions that may be produced by the article. When the spectral signal of detected emissions is within the authenticating parameter range of the detection apparatus that corresponds with the authenticating phosphor compound (referred to as the "detection parameter space"), the article may be considered authentic. Conversely, when the authentication equipment fails to sense signals expected within the detection parameter space, the article may be considered unauthentic.

The above-described techniques are highly effective at detecting and thwarting relatively unsophisticated forgery and counterfeiting activities. However, individuals with the appropriate resources and equipment may be able to employ spectrometry techniques in order to determine the components of some phosphor compounds. The phosphor compounds may then be reproduced and used with unauthentic articles, thus compromising the authentication benefits that may otherwise be provided by a particular phosphor compound. Accordingly, although a number of phosphor compounds have been developed to facilitate article authentication in the above-described manner, it is desirable to develop additional compounds, unique ways of using such compounds with articles, and techniques for authenticating articles, which may render forgery and counterfeiting activities more difficult, and/or which may prove beneficial for identifying and tracking articles of particular interest. Furthermore, other desirable features and characteristics of the present invention will become apparent from the subsequent detailed description of the invention and the appended claims, taken in conjunction with the accompanying drawings and this background of the invention.

BRIEF SUMMARY

An embodiment of a luminescent material includes first particles of a first inorganic host lattice and second particles of a second inorganic host lattice. The first particles have at least one first substance dispersed within the first inorganic host lattice. The first particles are capable of producing first emissions having one or more first emission peaks at one or more first wavelengths. The one or more first wavelengths include at least one first visible wavelength within the visible spectrum, and the first emissions at the first visible wavelength have a first decay half-life that is long enough for the first emissions at the first visible wavelength to be perceptible to the human eye for a first time period that begins when appropriate excitation of the luminescent material is discontinued. The second particles have at least one second substance dispersed within the second inorganic host lattice. The second particles are capable of producing second emissions having one or more second emission peaks at one or more second wavelengths. The one or more second wavelengths include at least one second visible wavelength within the visible spectrum. The second visible wavelength is different from the first visible wavelength, and the second emissions at the second visible wavelength have a second decay half-life that is longer than the first decay half-life by a decay time difference that is sufficient for the second emissions at the second visible wavelength to be perceptible to the human eye for a second time period that begins after the first time period.

An embodiment of an article includes first particles of a first inorganic host lattice and second particles of a second inorganic host lattice. The first particles have at least one first substance dispersed within the first inorganic host lattice. The first particles are capable of producing first emissions having one or more first emission peaks at one or more first wavelengths. The one or more first wavelengths include at least one first visible wavelength within the visible spectrum, and the first emissions at the first visible wavelength have a first decay half-life that is long enough for the first emissions at the first visible wavelength to be perceptible to the human eye for a first time period that begins when appropriate excitation of the luminescent material is discontinued. The second particles have at least one second substance dispersed within the second inorganic host lattice. The second particles are capable of producing second emissions having one or more second emission peaks at one or more second wavelengths. The one or more second wavelengths include at least one second visible wavelength within the visible spectrum. The second visible wavelength is different from the first visible wavelength, and the second emissions at the second visible wavelength have a second decay half-life that is longer than the first decay half-life by a decay time difference that is sufficient for the second emissions at the second visible wavelength to be perceptible to the human eye for a second time period that begins after the first time period.

An embodiment of a method for authenticating an article includes providing excitation energy to the article by moving an article and an excitation source with respect to each other, and determining whether emissions from a first portion of the article correspond to a first color and emissions from a second portion of the article correspond to a second color that is different from the first color. When the emissions from the first portion of the article and the emissions from the second portion of the article simultaneously do not correspond to the first color and the second color, the method includes determining that the article is not authentic.

BRIEF DESCRIPTION OF THE DRAWINGS

Embodiments of the present invention will hereinafter be described in conjunction with the following figures, wherein like numerals denote like elements, and wherein.

DETAILED DESCRIPTION

The following detailed description of various embodiments of the invention is merely exemplary in nature and is not intended to limit the inventive subject matter or the application and uses of the inventive subject matter. Furthermore, there is no intention to be bound by any theory presented in the preceding background or the following detailed description.

Embodiments discussed in detail below include luminescent materials, methods for producing luminescent materials, articles that include luminescent materials, and methods for identifying luminescent materials in the context of article authentication. More specifically, embodiments of luminescent materials include particles of two or more inorganic host lattices, each of which includes a substance with one or more emitting ions. The emitting ions in each substance are capable of producing human-observable emissions (i.e., emissions from each of the emitting ions have decay half-lives that are sufficiently long to allow human observation of the emissions). The embodiments of luminescent materials and methods and apparatus for their detection described below increase the diversity of available materials that may be used for authentication. The spectral signature and decay half-lives (or other decay-characterizing quantities) that characterize emissions from the luminescent material embodiments discussed herein may be used as observable or measurable quantities for the purpose of authentication.

More particularly, according to some embodiments, when exposed to an excitation source that moves relative to the luminescent material, a luminescent material may produce an emission having an emission "tail" that simultaneously includes multiple observable colors along the length of the tail. According to other embodiments, an article may include distinct regions, each with luminescent materials having different emitting ion ratios. After discontinuation of exposure of such an article to flood-type excitation across the distinct regions, the regions may produce emissions that simultaneously include different colors, shifting colors, and/or other visual or otherwise detectable effects. The multiple color emissions produced using the various embodiments make the phosphor compounds described herein particularly well suited for article authentication, although the phosphor compounds may be used for other purposes, as well.

Figure 1:
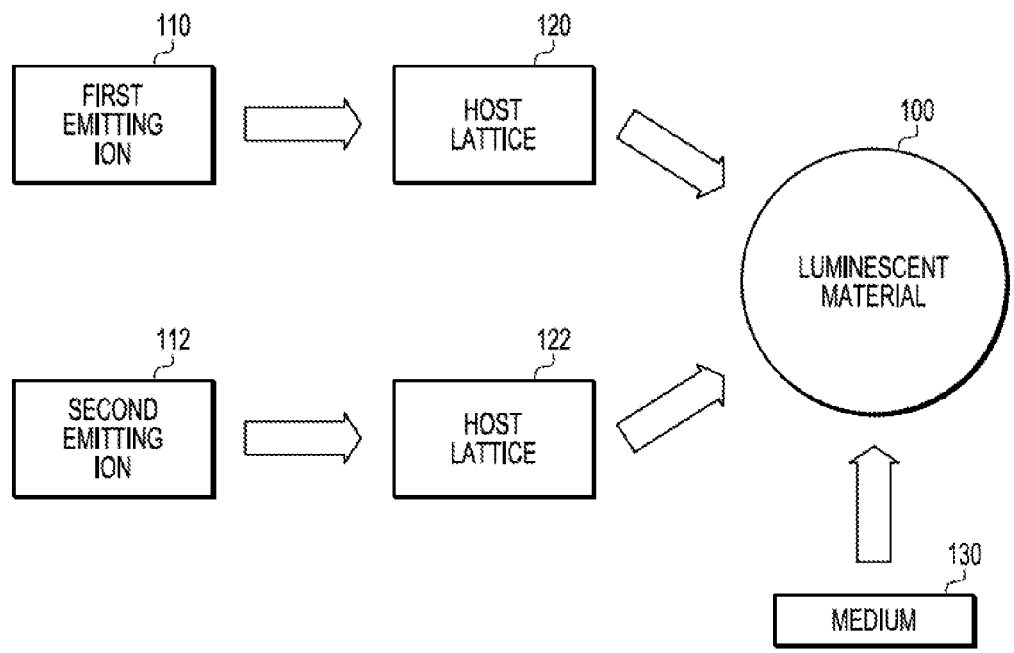
FIG. 1 depicts potential components of a luminescent material, according to various example embodiments.

FIG. 1 depicts potential components of a luminescent material 100, according to various example embodiments. According to an embodiment, luminescent material 100 includes, at least, a first substance with at least one first emitting ion 110 and a second substance with at least one second emitting ion 112. The term "ion," as used herein, is meant in the plural sense (e.g., a "first emitting ion" actually refers to a plurality of atoms (ions) of a first type). Although various embodiments of luminescent materials 100 are described herein as including first and second emitting ions 110, 112, it is to be understood that embodiments may include more than two emitting ions, as well. For example, either or both of the first and second substances may include multiple emitting ions, which are capable of producing emitted electromagnetic radiation in the visible and/or infrared regions of the electromagnetic spectrum. In addition, other embodiments may include one or more additional substances with one or more additional emitting ions, as will be described in more detail later.

According to various embodiments, the emitting ions 110, 112 include two different ions of elements selected from a group consisting of aluminum (Al), chromium (Cr), manganese (Mn), iron (Fe), copper (Cu), silver (Ag), tin (Sn), antimony (Sb), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lead (Pb), and mixtures thereof. The emitting ions 110, 112 have +3 valences, in an embodiment, although one or both of the emitting ions 110, 112 may have different valences (e.g., +2 and/or +4), in other embodiments.

According to an embodiment, the first substance with the first emitting ion 110 is included in a first inorganic host lattice 120, and the second substance with the second emitting ion 112 is included in a second inorganic host lattice 122. The host lattices 120, 122 comprise materials into which the first and second substances (including the first and second emitting ions 110, 112) are dispersed (i.e., the emitting ions 110, 112 are substituted for one or more ions of the host lattices 120, 122). More particularly, the host lattices 120, 122 are inorganic crystal lattices into which different chemical constituents may substitute at various positions within the lattice. In an alternate embodiment, the first and second substances with the first and second emitting ions 110, 120 may be substituted into a single host lattice, although such an embodiment is not discussed in detail herein.

Luminescent material 100 more specifically includes particles of the first and second host lattices 120, 122 with the first and second substances. As will be described in more detail later, upon exposure to appropriate excitation energy, the particles of each host lattice 120, 122 emit visible light having wavelengths that are governed not only by the host lattice itself, but also by the substances (with the first and second emitting ions 110, 112) dispersed into each host lattice 120, 122. The substances can include one or several materials that cause an energy transfer cascade that results in an emission wavelength pattern (e.g., including one or several emission peaks) issuing from the host lattice 120, 122.

The ions of the host lattices 120, 122 that may be replaced are ions that may be substituted by one or more emitting ions 110, 112 and by one or more sensitizing ions, if included, up to and including 100% substitution (although 100% substitution is rare since most emitting ions are concentration quenched well below a 100% substitution level). More specifically, the total concentration of emitting ions 110, 112 substituted in host lattices 120, 122 may be in a range from about 0.095 atomic percent to 100 atomic percent. The emitting ions 110, 112 may be substituted at very low substitution percentages (e.g., doped at less than 1%), medium substitution percentages (e.g., from 1% to 20%), or high substitution percentages (e.g., from 20% to 100%). As used herein, the term "substituted" means substituted at any percentage, including low, medium, and high substitution percentages. The amount of each ion substituted into a host lattice 120, 122 is generally described in terms of atomic percent, where the number of ions of the host lattice 120, 122 that may be replaced by emitting and/or sensitizing ions is equal to 100%. An ion of a host lattice 120, 122 that allows for replacement with emitting and/or sensitizing ions typically has similar size, similar loading, and similar coordination preference as the ions they will be replaced with.

The first host lattice 120 and the second host lattice 122 may be a same type of inorganic material or different types of inorganic materials. For example, in various embodiments, the first and second host lattices 120, 122 include one or more materials selected from a group consisting of oxides, fluorides, sulfides, oxysulfides, halides, borates, gallates, phosphates, vanadates, oxyhalides, aluminates, molybdates, tungstates, garnets, germanates, chlorophosphates, niobates, and mixtures thereof, although other host lattice materials may be used, as well. For example, but not by way of limitation, either or both of host lattices 120, 122 may have an empirical formula selected from a group consisting of $BaMg_2Al_{16}O_{27}$, ZnS, $Y_3Al_5O_{12}$ (YAG), $Y_2O_2S$, $Gd_3Ga_5O_{12}$, $Y_3Ga_5O_{12}$ (YGG), $Y_3Fe_5O_{12}$ (YIG), YIG:YGG, mixtures thereof, or other materials. In another embodiment, the first and second host lattices 120, 122 include a silicate, optionally in combination with any of the aforementioned materials. For example, but not by way of limitation, either or both of host lattices 120, 122 may have an empirical formula of $Zn_2SiO_4$, $Me_3MgSi_2O_8$ (where Me is an alkaline earth element (e.g., calcium, strontium, barium or any combination thereof)), or a combination thereof, optionally in combination with any of the aforementioned materials.

The first and second emitting ions 110, 112 may receive energy for subsequent radiation through one or more of multiple mechanisms. For example, either or both of the first and second emitting ions 110, 112 may be capable of directly absorbing exciting radiation, and the first and/or second emitting ions 110, 112 may thereafter radiate at least some of the absorbed energy (typically at a different and longer wavelength from the exciting radiation). Alternatively, the host material or an ion thereof (e.g., a vanadate ion) may be capable of absorbing excitation energy directly, and transferring energy to the first and/or second emitting ions 110, 112. In other situations, the first and/or second host lattices 120, 122 may include one or more "sensitizing ions" (e.g., a transition metal ion or rare earth metal ion), which may absorb exciting radiation within their appropriate absorption bands, and may transfer at least some of that energy directly or via cascade through one or more other ions to the first and/or second emitting ions 110, 112. The first and/or second emitting ions 110, 112, in turn, may produce detectable emissions as a result of having received the energy from the sensitizing ion(s).

For conciseness, the "visible portion of the electromagnetic spectrum" is referred to herein as the "visible spectrum," and a wavelength within the visible spectrum is referred to herein as a "visible wavelength." According to an embodiment, first host lattice 120 with the first emitting ion 110 is capable of producing emissions having one or more first emission peaks at one or more first wavelengths, where the one or more first wavelengths include at least one first visible wavelength. In addition, the second host lattice 122 with the second emitting ion 112 is capable of producing emissions having one or more emission peaks at one or more second wavelengths, where the one or more second wavelengths include at least one second visible wavelength. The second visible wavelength is different from the first visible wavelength. According to an embodiment, the first visible wavelength and the second visible wavelength are different by at least 20 nanometers (nm), with an upper limit of the difference being such that both the first and second visible wavelengths still are within the visible spectrum. According to another embodiment, the first visible wavelength and the second visible wavelength are different by at least 10 nm. According to yet another embodiment, the first visible wavelength and the second visible wavelength are different by at least 2 nm. According to further embodiments, the first visible wavelength corresponds to a first color, and the second visible wavelength corresponds to a second color that is different from the first color.

Although the description herein primarily discusses a luminescent material having particles of two host lattices with two substances dispersed therein, in other embodiments, a luminescent material may include one or more additional particles of one or more additional host lattices having one or more additional substances dispersed within the one or more additional inorganic host lattices. The additional particles may be capable of producing one or more additional emissions having one or more additional emission peaks at one or more additional wavelengths, wherein the one or more additional wavelengths include one or more additional visible wavelengths. The one or more additional visible wavelengths are different from the first visible wavelength and the second visible wavelength (e.g., the additional visible wavelengths correspond to colors that are different from the first and second colors).

Figure 2:
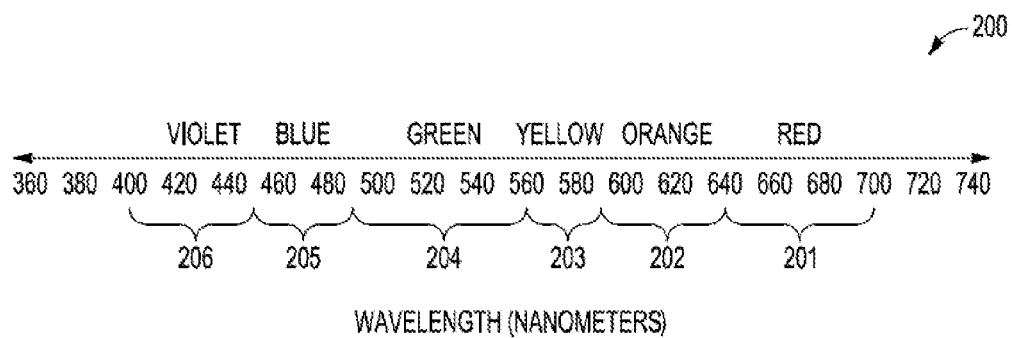
FIG. 2 illustrates the visible spectrum, showing wavelength ranges that correspond to different visible colors.

FIG. 2 illustrates the visible spectrum 200, showing wavelength ranges that correspond to different visible colors. More particularly, the visible spectrum 200 includes wavelength ranges corresponding to red (i.e., range 201 from about 700 nm to about 635 nm), orange (i.e., range 202 from about 635 nm to about 590 nm), yellow (i.e., range 203 from about 590 nm to about 560 nm), green (i.e., range 204 from about 560 nm to about 490 nm), blue (i.e., range 205 from about 490 nm to about 450 nm), and violet (i.e., range 206 from about 450 nm to about 400 nm). In an embodiment, the first and second emitting ions 110, 112 produce emissions of different colors selected from red, orange, yellow, green, blue, and violet.

Both the first and second emitting ions 110, 112 produce emissions that are perceptible to the human eye. As used herein, emissions may be considered to be "perceptible to the human eye" when the emissions are within the visible portion of the electromagnetic spectrum, and the emissions have decay half-lives that are at least about 10 milliseconds (ms). When an emission is no longer perceptible to the human eye, the emission is considered to have "substantially decayed." In quantifiable terms, an emission may be considered to have "substantially decayed" when the emission has an intensity (or integrated intensity) of less than about 10 percent of a maximum intensity within a particular emission band (e.g., an emission band encompassing the first or second wavelength). As used herein, an "emission band" is defined to mean a continuous range of wavelengths of the electromagnetic spectrum within which concentrated, non-negligible (e.g., detectable) emissions occur from an emitting ion. For any particular emitting ion, an "emission band" is bounded by a lower wavelength below which emissions are negligible for that ion, and an upper wavelength above which emissions are negligible for that ion.

The emissions produced by the first emitting ion 110 have a first decay half-life that is long enough for the emissions to be perceptible to the human eye for a first time period that begins when appropriate excitation of the luminescent material 100 is discontinued. The emissions produced by the second emitting ion 112 have a second decay half-life that is longer than the first decay half-life by a time difference that is sufficient for the second emissions to be perceptible to the human eye for a second time period that begins at the end of the first time period. In embodiments of luminescent materials that include one or more additional particles of one or more additional host lattices (resulting in additional emissions at additional visible wavelengths), the additional emissions at the one or more additional visible wavelengths have one or more decay half-lives that are different from the first decay half-life and the second decay half-life by one or more decay time differences that are sufficient for the additional emissions at the one or more additional visible wavelengths to be perceptible to the human eye for one or more additional time periods that begin after the first time period and the second time period.

Figure 3:
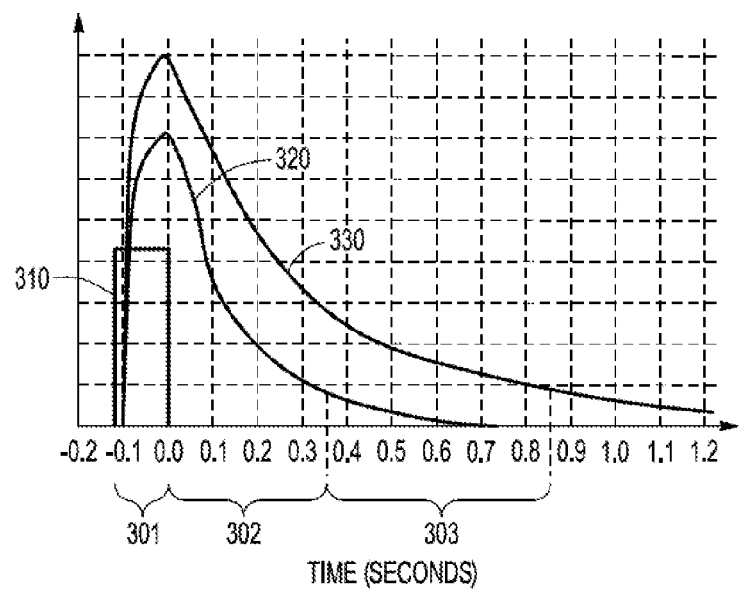
FIG. 3 is a graph depicting emission intensity versus time for emissions from two emitting ions of a luminescent material, in accordance with an example embodiment.

FIG. 3 is a graph depicting emission intensity versus time for emissions from two emitting ions (e.g., emitting ions 110, 112, FIG. 1) of a luminescent material (e.g., luminescent material 100, FIG. 1), in accordance with an example embodiment. More particularly, trace 320 represents the decay characteristics for a first emitting ion (e.g., first emitting ion 110, FIG. 1) of a luminescent material, and trace 330 represents the decay characteristics for a second emitting ion (e.g., second emitting ion 112, FIG. 1) of the luminescent material. Trace 310 represents an exciting radiation pulse (i.e., the luminescent material is exposed to the exciting radiation for an excitation time period 301 beginning at t=−10 milliseconds, and the exciting radiation is discontinued at t=0). The exciting radiation may be provided by any of a number of radiation sources (e.g., LEDs, laser diodes, or other radiation sources), as long as the exciting radiation has sufficient energy at one or more wavelengths that are appropriate to directly or indirectly excite the first and second emitting ions to a state at which they may produce observable emissions.

Upon removal of the exciting radiation (trace 310), the intensities of the first and second ion emissions decay over time, and the rate of decay for each of the emitting ions can be characterized by a decay half-life or a decay time constant, as mentioned above. For example, for a simple exponential decay in emission intensity, a decay time constant can be represented by the constant τ in the equation:

$$I(t)=I_0 e^{-t/\tau},\qquad\text{(Equation 1)}$$

where t denotes time, I(t) denotes the emission intensity at time t, and $I_0$ denotes the emission intensity at t=0 (e.g., t=0 may correspond to the instant when the provision of exciting radiation is discontinued). Although the emission intensity for some luminescent materials may decay according to the above, simple exponential formula, the emission intensity for other luminescent materials may be affected by multiple exponential decays (e.g., when multiple mechanisms affecting the decay are present).

Assuming a simple exponential decay, and as traces 320, 330 indicate, the emitted radiation from the second emitting ion (trace 330) has a relatively long persistence (i.e., a relatively large decay half-life) when compared with the persistence of the emitted radiation (trace 320) from the first emitting ion. For example, the first emitting ion may have a decay half-life in the range of about 10 to about 100 milliseconds or more, whereas the second emitting ion may have a decay half-life in a range of about 50 milliseconds or more (e.g., on the order of seconds, minutes or hours). In any event, the persistence of the emitted radiation from both the first and second emitting ions is sufficient for the emissions to be perceptible by a human observer, and the persistence of emitted radiation from the second emitting ion is longer than the persistence of emitted radiation from the first emitting ion by a significant time difference (e.g., at least about 10 milliseconds).

When the excitation energy is discontinued, emissions from both the first and second emitting ions may be observable during the first time period 302. After the emissions from the first emitting ion (trace 320) have substantially decayed to a level that they are no longer observable to the human eye (e.g., at the end of the first time period 301), the emissions from the second emitting ion (trace 330) continue to be observable to the human eye (e.g., until conclusion of a second time period 303, when the emissions from the second emitting ion have substantially decayed).

Because the first and second emitting ions 110, 112 produce emissions having different wavelengths within the visible portion of the electromagnetic spectrum (e.g., differently colored emissions), emissions from the luminescent material 100 during the first time period include a combination of emissions at the first and second emission wavelengths (e.g., a combination of two different colors). Conversely, during the second time period, emissions from the luminescent material 100 during the second time period include only emissions at the second emission wavelength (e.g., only a single color). As will be described in more detail later, this feature of the various embodiments enables interesting observable emissions to be produced by articles within which the luminescent material embodiments are incorporated.

Referring again to FIG. 1, any combination of the first host lattice 120 (with the first emitting ion 110) and the second host lattice 122 (with the second emitting ion 112) may be considered to be the luminescent material 100. Alternatively, particles of the first and second host lattices 120, 122 (with their respective emitting ions 110, 112) may be combined with at least one medium 130 to form the luminescent material 100. In various embodiments, the particles of the first and second host lattices 120, 122 may be combined into a single medium 130, or the particles of the first and second host lattices 120, 122 may be combined into separate media. In the latter embodiment, the luminescent material 100 is considered to be any combination of the multiple media within which the particles of the first and second host lattices 120, 122 are included. For example, the multiple media (with their respective host lattices 120, 122) may be mixed together during fabrication of an article or a feature of an article, or the multiple media (with their respective host lattices 120, 122) may be included in distinct, but physically proximate portions of the article during its fabrication (e.g., in distinct layers or other components of an article, and/or in features or components that are in close physical proximity to each other (e.g., interspersed)).

For example, but not by way of limitation, a medium 130 within which either or both host lattices 120, 122 may be incorporated corresponds to a substrate of an article. In such embodiments, a medium 130 may include a base material for the substrate (e.g., paper, paper pulp, a polymer, plastic, plastic base resin, glass, metal, a textile, fiber, ceramic, wood, a slurry, and so on), and mixtures of these materials, with which either or both host lattices 120, 122 are combined. Alternatively, a medium 130 within which particles of either or both host lattices 120, 122 may be incorporated corresponds to a material that may be applied to (e.g., printed on, coated on, sprayed on, layered on, or otherwise adhered to or bonded to) the surface of an article substrate, or a feature that is embedded within a substrate (e.g., an embedded feature, a security thread, and so on). In such embodiments, a medium 130 may include an ink, ink additive, a base material for a layer or embedded feature, or another carrier. In still other embodiments, particles of the first and/or second host lattices 120, 122 may be incorporated or combined with other types of media 130 (e.g., glues, various liquids, gels, and so on).

Figure 4:
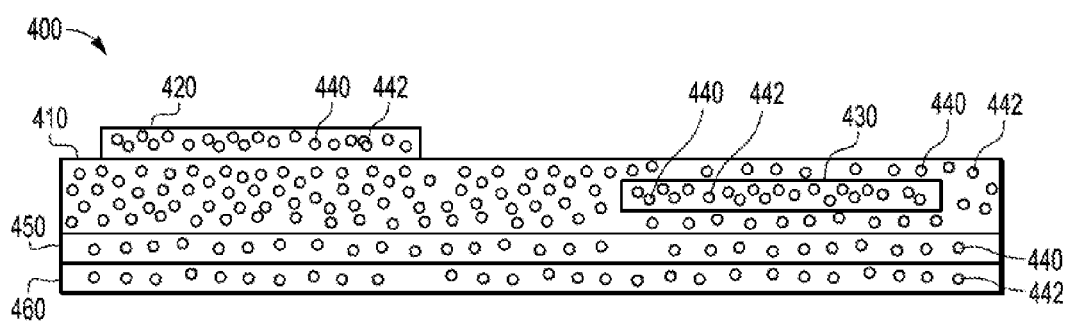
FIG. 4 is a cross-sectional, side view of an article that includes a substrate and one or more authentication features, according to an example embodiment.

FIG. 4 is a cross-sectional, side view of an article 400 that includes a substrate 410 and one or more authentication features 410, 420, 430, 450, 460, according to an example embodiment. Article 400 includes first and second emitting ions (e.g., first and second emitting ions 110, 112, FIG. 1) in particles 440, 442 of one or more host lattices (e.g., host lattices 120, 122). More specifically, embodiments of article 400 may include first particles 440 of a host lattice (e.g., host lattice 120, FIG. 1) within which one or more first emitting ions (e.g., first emitting ion 110, FIG. 1) are incorporated, and second particles 442 of a host lattice (e.g., host lattice 122, FIG. 1) within which one or more second emitting ions (e.g., second emitting ion 120, FIG. 1) are incorporated. For ease of description, particles 440, 442 are referred to below as "first ion particles" 440 and "second ion particles" 442 to indicate which type of emitting ion is included in each particle (i.e., the first or second emitting ions, respectively).

The first ion and second ion particles 440, 442 are incorporated in one or more media (e.g., medium 130, FIG. 1) from which the article 400 is formed. As indicated previously, the first ion and second ion particles 440, 442 may be included in a same medium that forms a portion of the article 400, or the first ion and second ion particles 440, 442 may be included in different media that form portions of the article 400. Either way, the medium or media with the first ion and second ion particles 440, 442 constitutes a luminescent material (e.g., luminescent material 100) that provides an authentication feature of the article 400. Although FIG. 4 shows a variety of types of authentication features, it is to be understood that an actual article may include more or fewer of such authentication features, and/or other types of authentication features. FIG. 4 is provided for the purpose of explanation and not of limitation. In addition, the various relative dimensions of the features 410, 420, 430, 450, 460 and particles 440, 442 may not be to scale in FIG. 4.

In various embodiments, article 400 may be any type of article selected from a group that includes, but is not limited to, an identification card, a driver's license, a passport, identity papers, a banknote, a check, a document, a paper, a stock certificate, a packaging component, a credit card, a bank card, a label, a seal, a token (e.g., for use in gambling and/or with a gaming or vending machine), a postage stamp, a liquid, a human, an animal, and a biological sample. Substrate 410 may be any of various types of substrates, and includes one or more materials selected from a group that includes, but is not limited to, paper, a polymer, glass, a metal, a textile, and a fiber.

Substrate 410, which may be rigid or flexible, may be formed from one or more layers or components, in various embodiments. The variety of configurations of substrate 410 are too numerous to mention, as the luminescent materials of the various embodiments may be used in conjunction with a vast array of different types of articles. Therefore, although a simple, unitary substrate 410 is illustrated in FIG. 4, it is to be understood that substrate 410 may have any of a variety of different configurations. For example, a substrate may be a "composite" substrate that includes a plurality of layers or sections of the same or different materials. For example, but not by way of limitation, a substrate may include one or more paper layers or sections and one or more plastic layers or sections that are laminated or otherwise coupled together to form the composite substrate (e.g., a paper layer/plastic layer/paper layer or plastic layer/paper layer/plastic layer composite substrate). In addition, although inanimate, solid articles are discussed herein, it is to be understood that an "article" also may include a human, an animal, a biological specimen, a liquid sample, and virtually any other object or material into or onto which a luminescent material of an embodiment may be included.

According to an embodiment, both the first ion particles 440 and the second ion particles 442 are evenly or unevenly dispersed within substrate 410. In such an embodiment, the substrate 410 with the incorporated first ion and second ion particles 440, 442 constitutes an authentication feature. Alternatively, substrate 410 may include either the first ion or second ion particle 440, 442, and another feature of article 400 that is applied to the surface or embedded within substrate 410 may include the other one of the first ion or second ion particle 440, 442.

According to other embodiments, both the first ion particles 440 and the second ion particles 442 may be evenly or unevenly dispersed within one or more surface-applied authentication features 420. A surface-applied authentication feature 420 may be, for example but not by way of limitation, a printed authentication feature or an authentication feature that includes one or more rigid or flexible materials into which or onto which either or both the first ion particles 440 and/or the second ion particles 442 are included. According to various embodiments, a surface-applied authentication feature 420 may have a thickness of about one micron or more, and a surface-applied authentication feature 420 may have a width and length that is less than or equal to the width and length of the substrate 410.

For example, but not by way of limitation, a surface-applied authentication feature 420 may comprise one or more inks, pigments, coatings, or paints that include either or both the first ion particles 440 and/or the second ion particles 442. For example, surface-applied authentication feature 420 may include one or more layers of a printed ink that includes both the first and second ion particles 440, 442, multiple layers of different printed inks, where a first ink of the different printed inks includes the first ion particles 440 and a second ink of the different printed inks includes the second ion particles 442. In still other embodiments, surface-applied authentication feature 420 may include multiple regions of different printed inks that are printed in close proximity to each other (e.g., interspersed) on the surface of substrate 410, where a first ink of the different printed inks includes the first ion particles 440 and a second ink of the different printed inks includes the second ion particles 442. In still other embodiments, a surface-applied authentication feature 420 may comprise one or more rigid or flexible feature substrates into which or onto which either or both the first ion particles 440 and/or the second ion particles 442 are included, where the feature substrate is then adhered or otherwise attached to a surface of the article substrate 410.

According to still other embodiments, both the first ion particles 440 and the second ion particles 442 may be evenly or unevenly dispersed within one or more embedded authentication features 430. An embedded authentication feature 430 comprises one or more rigid or flexible materials in which or onto which a luminescent material of an embodiment is included. For example, but not by way of limitation, an embedded authentication feature 430 may be configured in the form of a distinct, rigid or flexible substrate, a security thread, or another type of structure. According to various embodiments, an embedded authentication feature 430 may have a thickness in a range of about one micron up to the thickness of the substrate 410, and an embedded authentication feature 430 may have a width and length that is less than or equal to the width and length of the substrate 410.

According to still other embodiments, the first ion particles 440 may be included in a first layer 450 applied to a surface of substrate 410, and the second ion particles 442 may be included in a second layer 460 that is overlying or underlying the first layer 450. Alternatively, both the first and second ion particles 440, 442 may be combined within a single layer (not shown). In any event, the layer or layers 450, 460 may be formed from a transparent, semi-transparent, or opaque medium (e.g., a polymer, plastic, plastic base resin, glass, ceramic, and so on) suitable for layering on a surface of substrate 410 or on a surface of another layer.

The decay half-lives of emissions from the first ion particles 440 and the second ion particles 442 are affected by the substitution percentages (in atomic percent) of the first emitting ions and the second emitting ions within their respective host lattices. In addition, the ratios of the intensities of the emissions from the first and second emitting ions at any point on an article is affected by the relative concentration of first ion particles 440 and second ion particles 442 in any particular portion of the article. Both of these quantities may be controlled during the article manufacturing process. Accordingly, articles may be manufactured to produce emissions having pre-defined, and thus expected characteristics (e.g., in terms of wavelengths/colors, emission intensities, decay times, and so on). In addition, the various substitution percentages and relative concentrations intentionally may be varied in different areas of an article to produce interesting observable emission effects, as will be described in more detail below. When expected emissions are not observed (e.g., by a human observer or authentication equipment), an article may be considered to be unauthentic.

Figure 5:
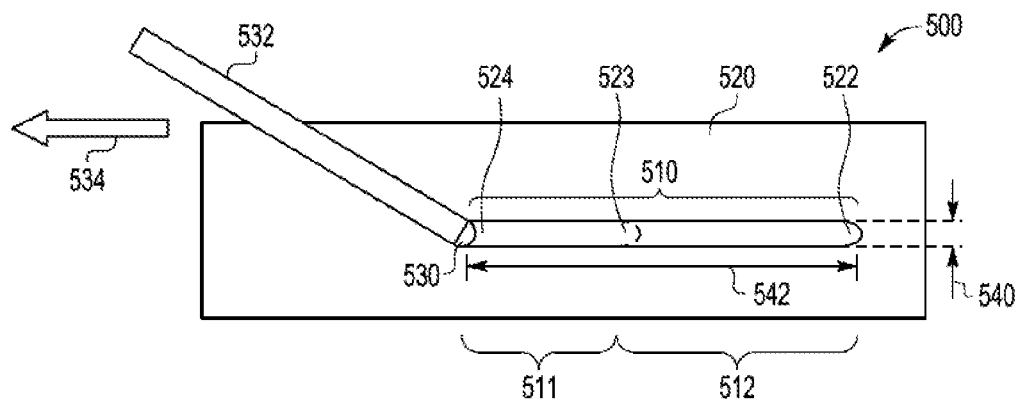
FIG. 5 is a top view of a portion of an article that includes a luminescent material of an embodiment, showing a multi-color emission tail visible on the article after exposure of the article to a moving excitation source, according to an example embodiment.

FIG. 5 is a top view of a portion of an article 500 that includes a luminescent material of an embodiment, showing a multi-color emission tail 510 that is visible on a surface 520 of the article 500 after exposure of the article 500 to a moving excitation source 530, according to an example embodiment. As defined herein, an "emission tail" is an emission from a region of an article, which results from exposure of the region to an excitation source that moves, relative to the article, over a period of time. Because the excitation source moves relative to the article, the emissions along a length of the tail correspond to different times from discontinuation of exposure to the excitation source, and thus to different points along the decay curves for the emissions, as will be clarified further below.

For example, article 500 may include one or more layers (e.g., layers 450, 460, FIG. 4) that include an even distribution, across a length of article 500, of first ion particles and second ion particles (e.g., particles 440, 442, FIG. 4). Alternatively, article 500 may include first and/or second ion particles in a surface-applied or embedded feature and/or within a substrate of article 500. Either way, when an excitation source 530 (e.g., an LED or other source incorporated into an LED pen 532 or other apparatus) is brought in proximity to a point 522 on the surface 520 of article 500, and moved with appropriate speed in a direction (indicated by arrow 534) parallel to the surface 520, an emission tail 510 is produced from a region of the surface 520 that corresponds to the path followed by the excitation source 530. Generally, a width 540 of the tail 510 corresponds to a width of the radiation produced by the excitation source 530. For a point-type excitation source, as illustrated in FIG. 5, the width 540 of the tail 510 may be relatively small, with respect to a width of the article 500. Conversely, for a line-type excitation source (e.g., an excitation source that produces exciting radiation in a line across a substantial portion or an entirety of the width of the article 500), the tail 510 may extend across a substantial portion or an entirety of the width of the article 500.

A length 542 of the tail 510 depends on the decay time constant for the emitting ion with the longest decay half-life and the speed at which the excitation source 530 moves with respect to the surface 520 of the article 500. For purposes of explanation, assume that a first emitting ion (e.g., emitting ion 110, FIG. 1) has a relatively short decay half-life (e.g., as indicated by trace 320, FIG. 3), and a second emitting ion (e.g., emitting ion 112, FIG. 1) has a relatively long decay half-life (e.g., as indicated by trace 330, FIG. 3). As discussed previously, and according to an embodiment, the first and second emitting ions are selected to produce differently-colored emissions so that the emission tail 510 includes regions 511, 512 of different colors (i.e., the tail 510 is a multi-color tail). A first region 511 closest to the excitation source 530 produces emissions that are relatively close, in time, to discontinuation of provision of exciting radiation to the area encompassed by the tail 510. For example, referring also to FIG. 3, the first region 511 may produce significant emissions from both the first and second emitting ions, such as during time period 302 (FIG. 3). Because the emissions from the first and second ions are differently colored (i.e., they are at different wavelengths), the total emissions from the first region 511 are a combination of the different colors. In addition, because the decay half-lives are different for the emissions from the first and second emitting ions, the relative contribution, with respect to the total emissions from the first region 511, of the emissions from the first emitting ion decreases along the length of the first region 511. In other words, at the closest point 524 to the excitation source 530 in the first region 511, the emission contributions of both the first and second ions are at a peak, and at the farthest point 523 from the excitation source 530 in the first region 511, the contribution of the first emitting ion to the total emissions approaches zero. However, the second emitting ion continues to produce emissions with sufficient intensity to be observable to the human eye, in an embodiment. Accordingly, in a second region 512 of the tail 510, significant emissions continue to be produced from the second emitting ion. For example, time period 303 (FIG. 3) indicates a period during which only the second emitting ion produces significant emissions in the second region 512.

As an example, a first ink medium was prepared with twenty percent, by weight, of $BaMg_2Al_{16}O_{27}$ particles, and a second ink medium was prepared with twenty percent, by weight of ZnS particles. The $BaMg_2Al_{16}O_{27}$ was doubly activated with twelve atomic percent europium and twelve atomic percent manganese, and was milled to a D50 particle size of about 7.44 microns and D95 of about 15.96 microns. The ZnS was activated with copper, and had a D50 particle size of about 5 microns and D95 of about 28 microns.

In isolation, the $BaMg_2Al_{16}O_{27}$ material (i.e., the $BaMg_2Al_{16}O_{27}$ particles with the manganese and europium in the first ink medium) produced an emission centered at about 600 nanometers (i.e., a magenta emission) when appropriately excited. More particularly, when excited with a 403 nanometer LED, the material exhibited about 50 percent of its peak emission intensity at about 13 milliseconds, 25 percent of its peak emission intensity at about 25 milliseconds, and 10 percent of its peak emission intensity at about 50 milliseconds. In addition, the ZnS material (i.e., the ZnS particles with the copper in the second ink medium), in isolation, produced an emission centered at about 533 nanometers (i.e., a green emission) when appropriately excited. More particularly, when excited with a 403 nanometer LED, the material exhibited about 50 percent of its peak emission intensity at about 170 milliseconds, about 25 percent of its peak emission intensity at about 450 milliseconds, and about 10 percent of its peak emission intensity at about 1200 milliseconds. As the above results show, the $BaMg_2Al_{16}O_{27}$ material has a relatively short decay half-life, and the ZnS material has a relatively long decay half-life.

A drawdown coating of a blend of the $BaMg_2Al_{16}O_{27}$ material and the ZnS material was made on banknote paper, and the coating was cured with an intense UV light source. The coated paper was applied to a rotating cylinder having a circumference of about 9 9/16 inches, and a 403 nm LED was mounted about 1/4 inch from the surface of the coated paper. When the LED was turned on and the cylinder was rotated, an emission tail was observed. An orange-yellow emission was observed in room light in about a 1 1/2 inch long region of the tail closest to the LED (e.g., akin to region 511, FIG. 5), representing a combination of the magenta and green emissions from the $BaMg_2Al_{16}O_{27}$ material and the ZnS material. Conversely, a green emission was observed in room light in a significantly longer region of the tail (i.e., a region at least 8 inches long) that began at the end of the first region (e.g., akin to region 512, FIG. 5), representing only the green emission from the ZnS material.

As the above description explains, various embodiments include articles that may exhibit multi-colored tails when luminescent materials proximate to the surface of the articles are excited with a moving excitation source of an appropriate excitation energy. As will be explained in conjunction with FIGS. 6 and 7, other embodiments include articles that emit different colors in different regions of the articles when the articles are excited with a flood-type excitation source (i.e., an excitation source that simultaneously floods an entire surface of the article with excitation energy).

Figure 6:
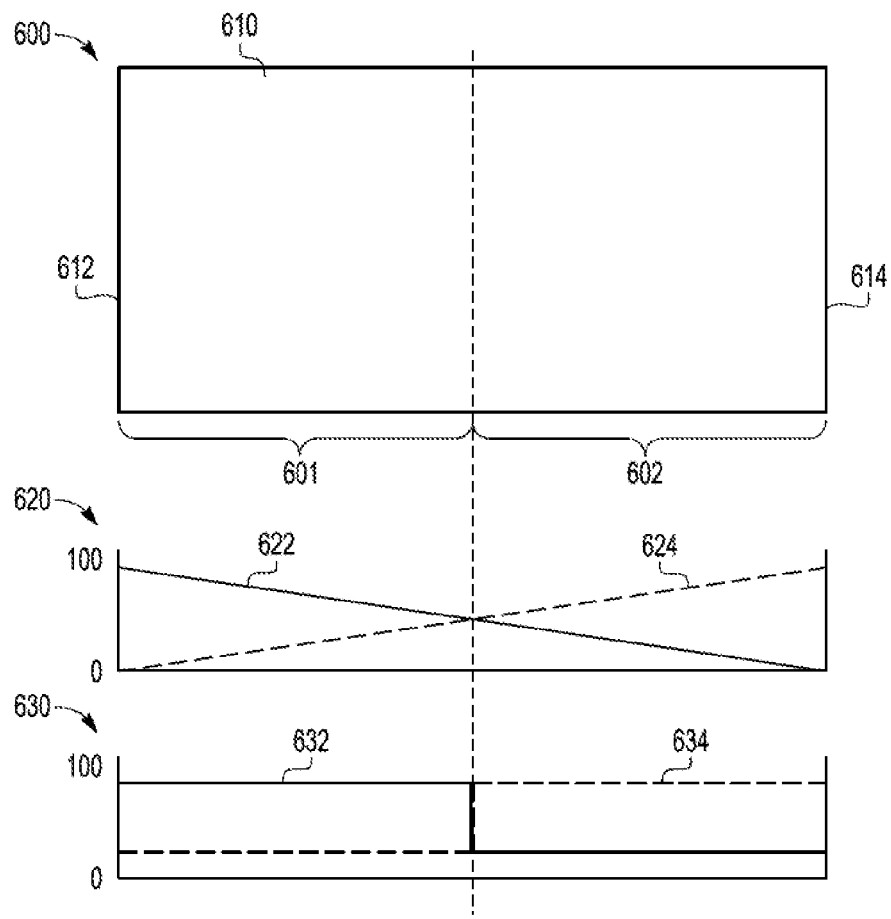
FIG. 6 is a top view of a portion of an article that includes a variable distribution of first and second emitting ions, according to an example embodiment.

For example, FIG. 6 is a top view of a portion of an article 600 that includes variable relative concentrations of first and second emitting ions across a surface 610 of the article 600, depicting variable color emissions visible on the article 600 after discontinuation of exposure to a flood-type excitation source, according to an example embodiment. For example, article 600 may include one or more layers (e.g., layers 450, 460, FIG. 4) that include an uneven relative concentration, across a length of article 600, of first ion particles and second ion particles (e.g., particles 440, 442, FIG. 4). Alternatively, article 600 may include uneven relative concentrations of first and/or second ion particles in a surface-applied or embedded feature and/or within a substrate of article 600.

For example, the relative concentration of first and second ion particles may have a gradient distribution across the length of article 600, as shown in graph 620, which plots relative concentrations of first emitting ions and second emitting ions (vertical axis) along a length (horizontal axis) of article 600. Trace 622 corresponds to an example relative concentration of a first emitting ion, and trace 624 corresponds to an example relative concentration of a second emitting ion across the length of article 600.

In a first region 601 of the article 600 that is proximate to a first edge 612 of the article, the first emitting ion has relatively high concentrations, which decrease with distance from the first edge 612, and the second emitting ion has relatively low concentrations, which increase with distance from the first edge 612. Because the intensity of the emissions is directly related to the concentration of an emitting ion, the initial intensity of emissions from the first emitting ion would be relatively high for that ion, but decreasing with distance from the first edge 612. Conversely, the initial intensity of emissions from the second emitting ion would be relatively low for that ion, but increasing with distance from the first edge 612. Compared with a second region 602 of the article 600, discussed below, the emissions from the first emitting ion initially would be relatively prominent in region 601, and the emissions from the second emitting ion initially would be relatively subdued in region 601, especially toward the first edge 612.

In a second region 602 of the article 600 that is proximate to a second edge 614 of the article, the first emitting ion has relatively low concentrations, which increase with distance from the second edge 614, and the second emitting ion has relatively high concentrations, which decrease with distance from the second edge 614. Accordingly, the initial intensity of emissions from the first emitting ion would be relatively low for that ion, but increasing with distance from the second edge 614. Conversely, the initial intensity of emissions from the second emitting ion would be relatively high for that ion, but decreasing with distance from the second edge 614. Compared with the first region 601 of the article 600, discussed above, the emissions from the first emitting ion initially would be relatively subdued in region 602, and the emissions from the second emitting ion initially would be relatively prominent in region 602, especially toward the second edge 614.

The varying relative concentrations of the first and second emitting ions, coupled with their different colors of emissions and different decay time constants, yields interesting visual effects (e.g., fading and shifting colors) across the surface of article 600. Although simple gradient distributions of the first and second ions having inverse properties are depicted in graph 620, it is to be understood that a variety of more complicated and different relative concentration differences could be implemented across an article. For example, rather than a continuous change in relative concentrations, step-wise changes in relative concentrations also could be implemented, as shown in graph 630. In that illustrated example, in the first region 601, the first emitting ion has a relatively high concentration that is consistent across the region 601 (trace 632), and the second emitting ion has a relatively low concentration that is consistent across the region 601 (trace 634). Conversely, in the second region 602, the first emitting ion has a relatively low concentration that is consistent across the region 602, and the second emitting ion has a relatively high concentration that is consistent across the region 602.

Again, numerous configurations of differing concentrations of first and second emitting ions could be implemented, in other embodiments, to provide a wide variety of visual effects. For example, the relative concentrations could be varied so that, upon discontinuation of appropriate, flood-type excitation, a multi-colored image or pattern initially may appear, which could change over time as the emissions from the first emitting ion died out. Alternatively, an article may include multiple surface-applied or embedded features that include different relative concentrations of first and second ions.

Figure 7:
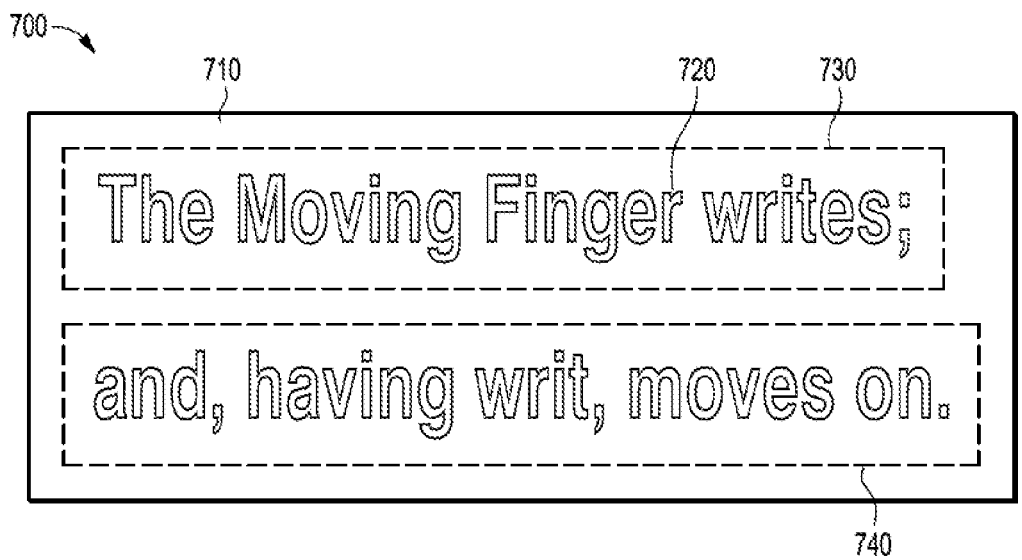
FIG. 7 is a top view of a portion of an article that includes printed text features with different concentrations of emitting ions various letters of the text, according to an example embodiment.

For example, FIG. 7 is a top view of a portion of an article 700 that includes printed text features on a surface 710 of the article, with different concentrations of emitting ions various letters 720 of the text, according to an example embodiment. For example, a first set 730 of the letters 720 may have a relatively high concentration of first emitting ions and a relatively low concentration of second emitting ions, and a second set 740 of the letters 720 may have a relatively low concentration of first emitting ions and a relatively high concentration of second emitting ions. As with the different regions 601, 602 of the article 600 of FIG. 6, the different relative concentrations of first and second emitting ions in the sets 730, 740 of letters 720 of article 700 result in the sets 730, 740 of letters exhibiting different emission characteristics after discontinuation of flood-type excitation, including different initial colors and/or intensities, and/or differently shifting colors.

Figure 8:
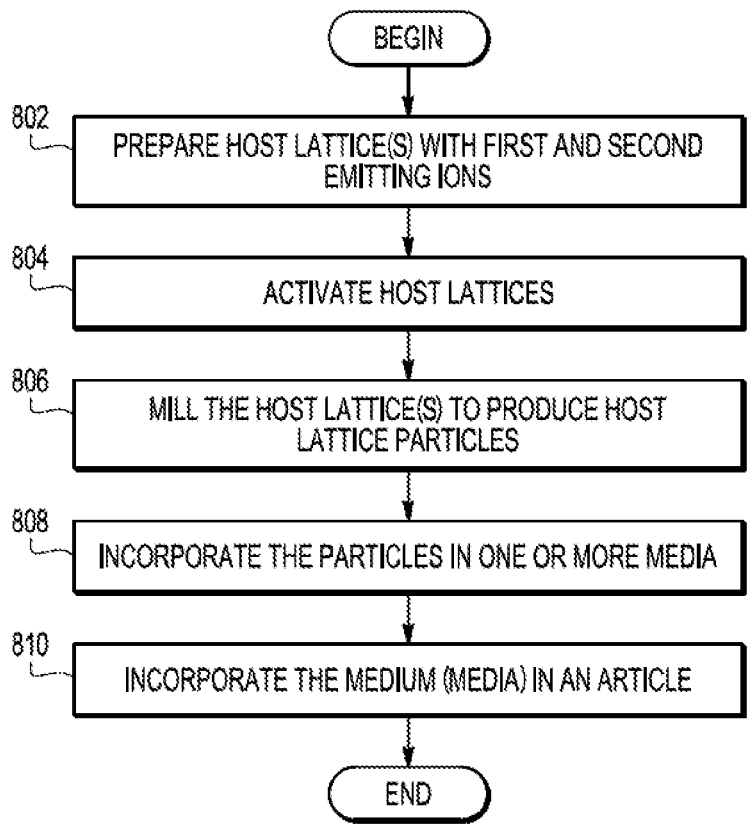
FIG. 8 is a flowchart of a method for producing a luminescent material and an article that includes the luminescent material, in accordance with an example embodiment.

FIG. 8 is a flowchart of a method for producing a luminescent material (e.g., luminescent material 100, FIG. 1) and an article (e.g., article 400, FIG. 4) that includes the luminescent material, in accordance with an example embodiment. The method begins, in block 802, by preparing one or more host lattices (e.g., host lattices 120, 122, FIG. 1) that include first and second emitting ions (e.g., emitting ions 110, 112, FIG. 1). Generally, a host lattice with emitting ions may be created using any of a number of conventional processes that are known to those of skill in the art. For example, formation of host lattices of the various embodiments may be achieved using solid state chemistry, as described below. More specifically, according to an embodiment, the host lattices are prepared by growing material crystals using components that include all of the elements of the lattices, typically in the form of oxides and other materials.

In addition, atom-for-atom replacements of substitutable elements in the host lattice for emitting ions may be achieved using oxides of those emitting ions (e.g., europium oxide ($Eu_2O_3$), neodymium oxide ($Nd_2O_3$), ytterbium oxide ($Yb_2O_3$), and so on). According to an embodiment, the ions in the emitting ion oxides have +3 valences. In order to substitute the emitting ions for the substitutable elements of the host lattices, some or all of the oxides for the substitutable elements are replaced with desired amounts of the emitting ion oxides, where replacement quantities are defined in terms of atomic number (i.e., indicating the percentage of host lattice ions replaced with emitting ions).

Once combined in the appropriate quantities (e.g., in quartz boats and/or alumina crucibles), the combination is activated, in block 804, by firing the combined components multiple times (e.g., four times, or some other number of times) at prescribed temperatures (e.g., temperatures in a range of about 500-1200 C, or a different range) for prescribed times (e.g., times in a range of about 30-60 minutes, or a different range), with powderizing processes being performed after each firing step. The resulting, powderized crystal thus forms a host lattice with one or more desired emitting ions.

Although solid state chemistry may be used to create the host lattices, as discussed above, in other cases, solution chemistry techniques may be used. Using solution chemistry, the various materials are dissolved, subsequently precipitated, and subsequently fired. Depending on the particular process used to create the host lattices, other materials may be included in forming the host lattices. For example, various fluxing agents and other pre-cursors may be included within the host lattices during their formation.

In block 806, the host lattices may be further milled and/or filtered to produce crystal particles of desired sizes. In block 808, the host lattice particles are incorporated into one or more media. For example, but not by way of limitation, a medium may correspond to a substrate of an article, or a medium may correspond to a material that may be applied to (e.g., printed on, coated on, sprayed on, or otherwise adhered to or bonded to) the surface of an article substrate, or a feature that is embedded within a substrate (e.g., an embedded feature, a security thread, and so on). In the former case, the host lattice particles may be incorporated into a substrate material, for example, by combining the host lattice particles with a base material (e.g., paper, paper pulp, a polymer, plastic, plastic base resin, glass, metal, a textile, fiber, ceramic, wood, a slurry, and so on) for the substrate, and/or by impregnating the substrate with a colloidal dispersion of the host lattice particles. Impregnation may be performed, for example, by a printing, dripping, coating or spraying process.

In embodiments in which the host lattice particles are incorporated into a material that may be applied to a surface of a substrate, the host lattice particles are mixed in with a composition (e.g., an ink, ink additive or other carrier). In embodiments in which the host lattice particles are incorporated into a feature that is embedded within a substrate, incorporation of the host lattice particles into the feature may be performed in a similar manner to incorporation of the host lattice particles into the substrate, as discussed above. More particularly, the host lattice particles may be mixed with a base material from which the embedded feature is formed. In still other embodiments, host lattice particles may be incorporated or combined with other media (e.g., glues, various liquids, gels, and so on).

In block 810, an article is produced that includes the host lattice-containing medium or media. For example, this may be accomplished by incorporating the medium or media in or on an article (e.g., article 400, FIG. 4). In embodiments in which the medium is the base material for the substrate, this step may be bypassed. Conversely, in embodiments in which the medium or media is applicable to a surface of the substrate, the medium or media may be printed onto one or more surfaces of the substrate in pre-determined locations. Conversely, when the medium or media corresponds to an embedded feature, the embedded feature is integrated with the substrate material when the substrate material is in a malleable form (e.g., when the material is a slurry, molten, or non-cured form). In any one of the above-described manners, an embodiment of a luminescent material may be incorporated into an article.

Figure 9:
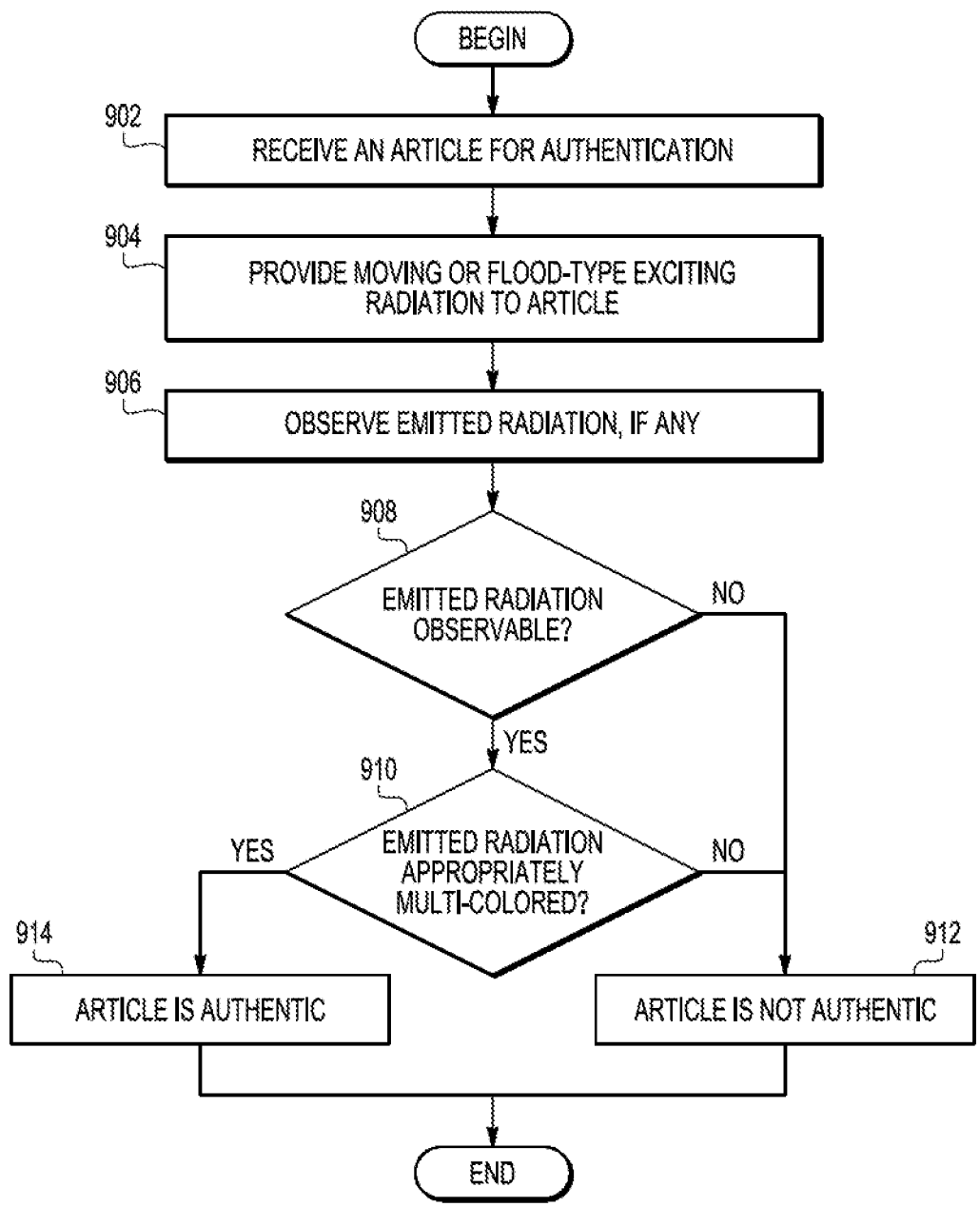
FIG. 9 is a flowchart of a method for performing authentication of an article manually, in accordance with an example embodiment.
Figure 10:
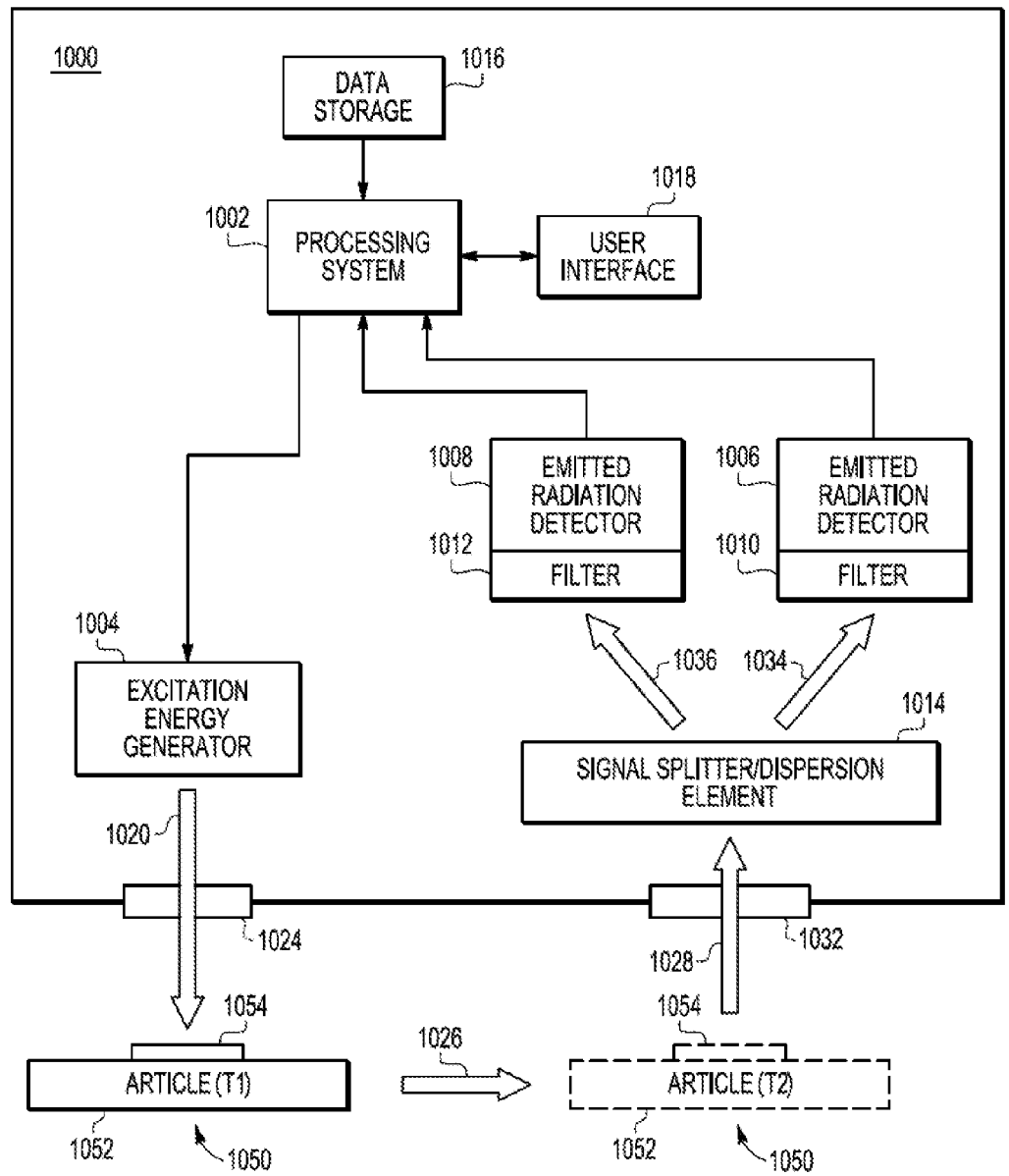
FIG. 10 is a system for authenticating an article, in accordance with an example embodiment.
Figure 11:
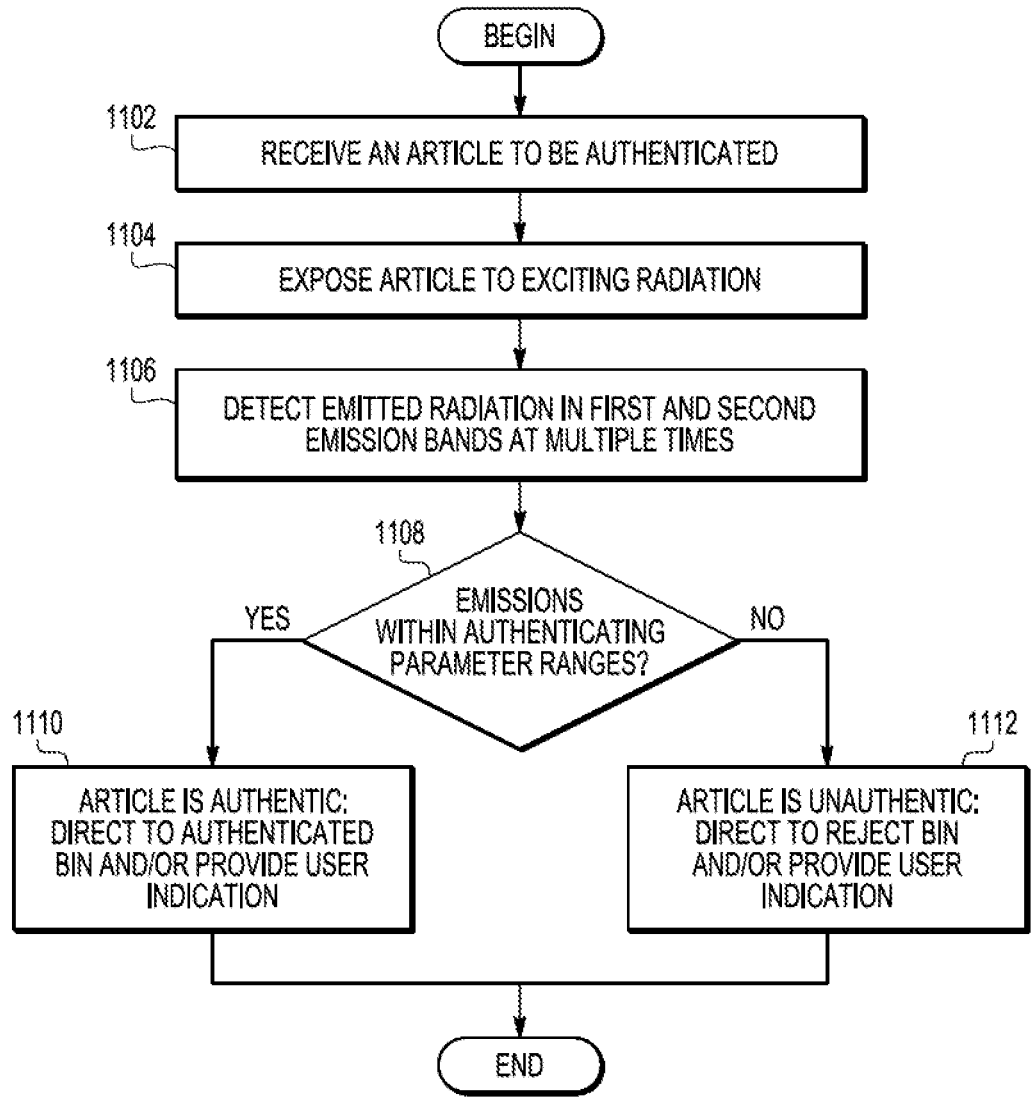
FIG. 11 is a flowchart of a method for performing authentication of an article using an authentication apparatus, in accordance with an example embodiment.

The absorption and emission properties of embodiments of luminescent materials discussed herein (e.g., luminescent material 100, FIG. 1) are consistent with their use in conjunction with security and authentication features. When the wavelengths of emission from the first and second emitting ions are within the visible portion of the electromagnetic spectrum, authentication may be performed manually (e.g., via human observation) or using suitably configured authentication equipment. When the wavelengths of emission from the first and second emitting ions are not within the visible portion of the electromagnetic spectrum, authentication may be performed using suitably configured authentication equipment. FIG. 9 depicts an embodiment of a method for performing authentication manually, and FIGS. 10 and 11 depict apparatus and methods for performing authentication using authentication equipment.

FIG. 9 is a flowchart of a method for performing authentication of an article (e.g., article 400, FIG. 4) manually, in accordance with an example embodiment. Essentially, a manual method for authenticating an article includes a human observer exciting the article with an excitation source, and observing whether radiation from the article as a result of the excitation has expected visual characteristics. According to an embodiment, the excitation source may include one or more LEDs, laser diodes or other light sources, which are capable of emitting exciting radiation having a wavelength or wavelengths in the absorption band(s) of one or more absorbing ions within the luminescent material. The absorbing ions may be the first and second emitting ions, in cases in which the first and second emitting ions may directly absorb the excitation energy. Alternatively, the absorbing ions may include one or more sensitizing ions or ions of the host lattice, which are capable of absorbing the excitation energy and transferring energy to the first and second emitting ions. The excitation source may provide a single wavelength of excitation energy when such excitation energy is capable of being directly or indirectly absorbed by both the first and second emitting ions. In such an embodiment, the excitation source may include a single light source. Alternatively, when the first and second emitting ions are capable of directly or indirectly absorbing excitation energy at different wavelengths, the excitation source may provide multiple wavelengths of excitation energy. In such an embodiment, the excitation source may include multiple light sources.

For a point-type excitation source, the excitation source may, for example, be incorporated into a small, portable housing (e.g., a pen-shaped housing, such as in FIG. 5), making it convenient for use by the human observer. Alternatively, for flood-type excitation sources, the excitation source may be incorporated into a larger housing, such as a box-like housing configured to allow the article to be placed into an interior chamber that is flooded with excitation energy from the excitation source.

A manual method for authenticating an article (e.g., article 400, FIG. 4) begins, in block 902, when the article is received by the human observer for authentication. The human observer brings the excitation source in proximity to or in contact with a surface of the article, and causes exciting radiation to be directed toward the article, in block 904. For example, for a point-type excitation source, the human observer may bring the excitation source into contact with (or just above) a point on the surface of the article, and draw the excitation source across the surface of the article (e.g., as indicated in FIG. 5). Alternatively, for a flood-type excitation source, the human observer may place the article in proximity to the excitation energy (e.g., slide the article into an internal chamber that is flooded with the excitation energy).

Upon discontinuation of the exciting radiation to a portion of the article or to the entire article, the human observer may observe whether emitted radiation, if any is perceptible in block 906. In the case of a point-type excitation source that is moved across the surface of the article, discontinuation of the exciting radiation to any particular point along the path of movement consists of the movement of the excitation source away from that point. As discussed previously in conjunction with FIG. 5, this may result in an emission tail (e.g., emission tail 510, FIG. 5) being observable on the surface of the article. Conversely, for a flood-type excitation source, discontinuation of the exciting radiation may include the human observer removing the article from an area at which the excitation energy is provided (e.g., removing the article from an internal chamber) or turning the excitation source off. As discussed previously in conjunction with FIGS. 6 and 7, this may result in a variety of visual effects being observable in different areas or features of the article.

The human observer may then make a series of determinations in order to form an opinion of whether or not the article is authentic. For example, a first determination may be made, in block 908, whether or not any emitted radiation or a sufficient intensity of emitted radiation is observable. If not, this would indicate that a luminescent material of an embodiment is not present in or on the article or that an insufficient quantity of the luminescent material is present in or on the article to indicate authenticity of the article. Accordingly, the human observer may determine, in block 912 that the article is not authentic, and the method may end.

When, however, the human observer determines that a sufficient intensity of emitted radiation is present, the human observer may make a further determination, in block 910, whether the emitted radiation is appropriately multi-colored. For example, when the emitted radiation is in the form of an emission tail (e.g., emission tail 510, FIG. 5), the human observer may determine whether the tail includes a first region having a first expected color (e.g., region 511, FIG. 5) and a second region having a second expected color (e.g., region 512, FIG. 5). Alternatively, the emitted radiation may be characterized by other visual effects, such as those discussed in conjunction with FIGS. 6 and 7, including simultaneous emission of different colors from different portions or features of the article, shifting colors, and so on. When the human observer determines that the emitted radiation is not appropriately multi-colored, the human observer may determine, in block 912 that the article is not authentic, and the method may end. When, however, the human observer determines that the emitted radiation is appropriately multi-colored, the human observer may determine, in block 914, that the article is authentic, and the method may end.

The above-described system and method may be particularly useful in situations in which a human observer is tasked with determining the authenticity of articles. As just a few examples, and not by way of limitation, the method may be useful for determining the authenticity of articles such as passports or other identification cards or papers (e.g., by security personnel at airports and other points of entry or departure), value documents, currency or credit cards (e.g., by clerks at banks or retail locations), driver's licenses (e.g., by police officers or others), and retail goods that are frequently subject to counterfeiting (e.g., clothing, handbags, books, shoes, and so on).

In other situations, benefits may be obtained by performing article authentication in a more rapid and automatic fashion (e.g., when authentic articles are being sorted from non-authentic articles by an automated system). Accordingly, embodiments also include systems and methods for performing automatic authentication of articles.

FIG. 10 is a system 1000 for authenticating an article 1050, in accordance with an example embodiment. System 1000 includes a processing system 1002, one or more excitation energy generators 1004, one or more emitted radiation detectors ("detectors") 1006, 1008 with associated optical filters ("filters") 1010, 1012, a signal splitter/dispersion element 1014, data storage 1016, and a user interface 1018, according to an embodiment. Processing system 1002 may include one or more processors and associated circuitry, which is configured to implement control and analysis processes (e.g., in the form of executable software algorithms) associated with authenticating an article (e.g., article 1050).

Article 1050 includes a substrate 1052 and, optionally, a surface-applied or embedded authentication feature 1054, as discussed previously. In an embodiment, article 1050 is transported through the authentication system 1000 in a processing direction 1026, with an incident edge of article 1050 being presented to the system 1000 first, and a trailing edge of the article 1050 being presented to the system 1000 last. For example, at a first time (T1), article 1050 is passed under an excitation window 1024 of system 1000, and at a second, subsequent time (T2), article 1050 is passed under a detection window 1032 of system 1000. In an alternate embodiment, article 1050 may be moved into a stationary position within the authentication system 1000, and the excitation and detection windows 1024, 1032 may be moved over the stationary article 1050.

Either way, according to an embodiment, processing system 1002 is configured to provide control signals to the excitation energy generator 1004, which cause excitation energy generator 1004 to direct appropriate excitation energy 1020 toward article 1050 through excitation window 1024. As the article 1050 is moved under the excitation window 1024 (or the excitation window 1024 is moved over the article 1050), emitting ions in a luminescent material incorporated in the substrate 1052 or an authentication feature 1054, receive energy for subsequent radiation (using one or more energy absorption and/or transfer mechanisms).

In the control signals, processing system 1002 may specify the timing (e.g., start time, stop time, and/or duration) of the provision of excitation energy, and/or other parameters associated with the particular excitation energy to be generated (e.g., intensities and/or other parameters). Typically, the bandwidth of the excitation energy is pre-determined based on the excitation source(s) that is/are included as part of the excitation energy generator 1004 (e.g., the bandwidth of excitation energy produced by a selected LED or laser diode). As discussed previously, appropriate excitation energy for a luminescent material of an embodiment may be in one or more absorption bands, in various embodiments. The various timing and/or radiation generation parameters may be retrieved from data storage 1016, for example. Excitation energy generator 1004 may include, for example, one or more lasers, laser diodes, LEDs, incandescent filaments, lamps, or other excitation sources.

In addition to controlling excitation energy generator 1004, processing system 1002 is configured to provide control inputs to emitted radiation detectors 1006, 1008, which cause detectors 1006, 1008 to attempt to detect emissions 1028 emanating from article 1050 in response to the various emitting ions having absorbed (either directly or indirectly) at least some of the excitation energy 1020. For example, the article 1050 may produce emissions corresponding to multiple different wavelengths or colors, as previously discussed.

According to an embodiment, the emissions 1028 impinge upon the signal splitter/dispersion element 1014, which separates the emissions 1028 into beams 1034, 1036. One beam 1034 includes light at a first wavelength (e.g., a first color), and the second beam 1036 includes light at a second wavelength that is different from the first wavelength (e.g., a second and different color). Signal splitter/dispersion element 1014 directs the first beam 1034 toward one of detectors 1006, and directs the second beam 1036 toward the other of detectors 1008. According to an embodiment, signal splitter/dispersion element 1014 is configured to pass the first beam 1034 and to reflect the second beam 1036. For example, signal splitter/dispersion element 1014 may be an element selected from a group consisting of a polychromator, a prism, diffraction grating, a thin-film filter, an interference filter, a dichroic filter, a dichroic mirror, and a dichroic reflector. An advantage to such a signal splitter/dispersion element 1014 is that it enables both detectors 1006, 1008 simultaneously to receive components of an emission that emanated from a same area of the article 1050, thus maximizing correlation of the resulting intensity measurements.

Each emitted radiation detector 1006, 1008 may include, for example, a spectral filter 1010, 1012, one or more electro-optical sensors, photomultiplier tubes, avalanche photodiodes, photodiodes, charge-coupled devices, charge-injection devices, photographic films, or other detection devices. In a particular embodiment, each emitted radiation detector 1006, 1008 includes a spectral filter 1010, 1012 positioned between the signal splitter/dispersion element 1014 and a photodetector. The spectral filters 1010, 1012 are configured to filter the beams 1034, 1036 before they are provided to detectors 1006, 1008, so that emissions only within an emission band (i.e., a subset of the entire spectrum) actually impinges upon the active area of each detector 1006, 1008. The spectral filters 1010, 1012 may include, for example, long pass, bandpass, or other types of filters configured to pass light only within a spectral band of interest, and to reject all other light.

Each of detectors 1006, 1008 has sensitivity within a spectral band of interest, and accordingly may detect light passing through the spectral filter 1010, 1012 that is within that spectral band. According to an embodiment, detector 1006 is configured to detect emissions within a channel corresponding to a first band of interest (a band that includes a first wavelength associated with a first color), and detector 1008 is configured to detect emissions within a channel corresponding to a second band of interest (a band that includes a second wavelength associated with a second color). The detectors 1006, 1008 may be of the same or different types or classes. For example, either or both of detectors 1006, 1008 may include a silicon detector, an indium-gallium-arsenide (InGaAs) detector (e.g., a telecom type or extended InGaAs), a lead-sulfide detector, a lead-selenide detector, a germanium detector, an indium-antimonide detector, an indium-arsenide detector, a platinum-silicide detector, an indium-antimonide detector, or another type of detector. In an alternate embodiment, a single detector may be employed, which is capable of detecting emissions in all bands of interest. In such an embodiment, signal splitter/dispersion element 1014 may be excluded from system 1000.

Each detector 1006, 1008 produces an electronic signal that is proportional to the intensity of the collected radiation that impinges on the active area of the detector 1006, 1008. More particularly, each detector 1006, 1008 produces a signal (e.g., one or more digitized intensity values) representing an integrated intensity of the emissions received by the detector 1006, 1008 along substantially all or a portion of the length of the article (e.g., between an incident and trailing edge of the article). Desirably, when multiple detectors 1006, 1008 are used in the system (e.g., as in the system 1000 of FIG. 10), the values of the integrated intensity are electronically captured by each detector 1006, 1008 at the same time, although this is not a requirement.

Each emitted radiation detector 1006, 1008 may digitize intensity values at one or more pre-selected intervals (e.g., starting at t=0, and then every 0.1 milliseconds thereafter, for multiple intervals). In addition, each emitted radiation detector 1006, 1008 provides information to processing system 1002 (e.g., the digitized intensity values), which enables the temporal, spectral, and positional properties of the emissions 1028 to be characterized. For example, emitted radiation detector 1006 produces a series of values corresponding to intensities of emitted radiation in a first band that includes a first wavelength associated with a first color, and emitted radiation detector 1008 produces a series of values corresponding to the intensities of emitted radiation in a second band that includes a second wavelength associated with a second color. Each value or sets of values from detectors 1006, 1008 may be tagged or otherwise associated with information indicating a location of the detected emissions (e.g., a linear distance from the incident edge of the article) and/or a time when the emissions were detected (e.g., a time from discontinuation of provision of the corresponding excitation energy).

Processing system 1002 is configured to analyze such information, upon its receipt, in order to determine whether or not the temporal, spectral, and positional properties of any detected radiation correspond to the temporal, spectral, and positional properties of an authentic article. As will be described in more detail in conjunction with FIG. 11, authenticating parameters for the system 1000 include parameters selected from a group consisting of: emission intensities (or integrated intensities) in two or more distinct emission bands or at two or more distinct wavelengths; emission decay time constants in the two or more emission bands or at the two or more distinct wavelengths; and ratio of emission intensities (or integrated intensities) between emissions in the two or more emission bands or at the two or more distinct wavelengths. Additional authenticating parameters may be defined, as well.

Ranges of authenticating parameters that correspond with an authentic article define the detection parameter space of the system 1000. In an embodiment, processing system 1002 determines whether the values produced by detectors 1006, 1008 that relate to the authenticating parameters fall within the detection parameter space. In other words, processing system 1002 compares the values with ranges defining the detection parameter space to determine whether the values fall within those ranges. For example, regarding the authentication parameter corresponding to two or more emission bands (or wavelengths) corresponding to multiple colors, a table of intensity value ranges may be defined and stored in data storage 1016. In order to analyze a particular intensity value (e.g., an intensity value from detector 1006 or 1008), processing system 1002 may retrieve a pre-defined intensity range from the table, and may compare the intensity value with the range to determine whether the value falls within the range. Such analyses may be performed for intensity values at multiple locations along the length of the article. As another example, regarding the authentication parameter corresponding to the ratio of emission intensities in two or more emission bands (or wavelengths), a range of acceptable ratios may be defined and stored in data storage 1016. Processing system 1002 may calculate the ratio of emission intensities in the two or more emission bands (or at the two or more wavelengths) (e.g., based on intensity values from detectors 1006, 1008), retrieve the pre-defined, acceptable ratio range from data storage 1016, and may compare the ratio with the range to determine whether the ratio falls within the range. Values corresponding to the other authentication parameters may be similarly analyzed.

When the analysis indicates that the values corresponding with the authenticating parameters fall within the detection parameter space to within an acceptable degree of accuracy, processing system 1002 may identify the article 1050 as being authentic. Conversely, when the analysis indicates that the values corresponding with the authenticating parameters do not fall within the detection parameter space to within an acceptable degree of accuracy, processing system 1002 is configured to identify the article 1050 as being unauthentic.

When the temporal and/or spectral properties of detected radiation correspond with an authentic article, processing system 1002 may take some action associated with identifying article 1050 as an authentic article. For example, processing system 1002 may send an electronic signal associated with authenticity to another component of the system or to an external system. In addition, processing system 1002 may send a signal to user interface 1018, which causes user interface 1018 to produce a user-perceptible indication of authenticity (e.g., a displayed indicia, a light, a sound, and so on). Processing system 1002 also may cause a routing component of system 1000 (not illustrated) to route article 1050 toward a route or bin assigned for authentic articles. Alternatively, when the temporal and/or spectral properties of the detected radiation do not correspond with an authentic article, processing system 1002 may take some action associated with identifying article 1050 as an unauthentic article. For example, processing system 1002 may send an electronic signal associated with unauthenticity to another component of the system or to an external system. In addition, processing system 1002 may send a signal to user interface 1018, which causes user interface 1018 to produce a user-perceptible indication of unauthenticity (e.g., a displayed indicia, a light, a sound, and so on). Processing system 1002 also may cause a routing component of system 1000 (not illustrated) to route article 1050 toward a route or bin assigned for unauthentic articles.

User interface 1018 may include any of a number of components that may be manipulated by a user to provide inputs to system 1000 (e.g., keyboards, buttons, touchscreens, and so on), or which may be controlled by processing system 1002 to produce user-perceptible indicia (e.g., display screens, lights, speakers, and so on). The above-described process may be initiated in response to user inputs provided through the user's interaction with user interface 1018, for example. Alternatively, the above-described process may be initiated automatically by the system 1000, such as when the article 1050 has been positioned in a location at which the excitation and detection processes may be performed.

FIG. 11 is a flowchart of a method for performing authentication of an article (e.g., article 1050, FIG. 10), in accordance with an example embodiment. For example, embodiments of the method depicted in FIG. 11 may be performed by an authentication system (e.g., authentication system 1000, FIG. 10). The method may begin, in block 1102, when an article to be authenticated is received by the authentication system. For example, an article may be routed (e.g., by a sorting or conveyor system) into the authentication system with an incident edge of the article first entering the authentication system. As another example, the article may be placed into an appropriate receptacle of the authentication system.

In block 1104, the article is exposed to excitation energy appropriate for the emitting, host lattice, and/or sensitizing ions in the luminescent material. To provide the excitation, the article may be routed to or past an excitation area (e.g., under excitation window 1024, FIG. 10), and the processing system (e.g., processing system 1002, FIG. 10) may send a control signal to an excitation energy generator (e.g., excitation energy generator 1004, FIG. 10) that causes the excitation energy generator to direct the excitation energy (e.g., excitation energy 1020, FIG. 10) toward the article. Alternatively, the excitation energy generator may continuously provide the first excitation energy or the first excitation energy may be modulated.

In block 1106, provision of the excitation energy to the article is discontinued, and the authentication system detects emissions within multiple bands (or at multiple wavelengths) from the article (e.g., by emitted radiation detectors 1006, 1008, FIG. 10). Emissions detection may be performed at one or more detection intervals, which are measured from the time that direction of the excitation energy toward the article was discontinued. According to an embodiment, the system is configured to detect emissions in at least two emission bands (or at at least two wavelengths) associated with at least two emitting ions (and at least two colors), although the system may be configured to detect emissions in other bands or at other wavelengths, as well. Discontinuation of the excitation energy may be accomplished either by turning the excitation energy generator off (e.g., in a system in which the article may remain stationary and the excitation energy is pulsed), or by routing the article away from the area where the excitation energy is being directed, and to a detection area (e.g., under detection window 1032, FIG. 10). In an alternate embodiment, provision of the excitation energy may continue while the system performs the detection processes described below.

Information quantizing the intensities of detected emissions within the multiple bands (or at the multiple wavelengths) is analyzed (e.g., by processing system 1002, FIG. 10). According to an embodiment, the information includes one or more series of digitized intensity values (e.g., from each of detectors 1006, 1008, FIG. 10) corresponding to intensities of emitted radiation in the multiple bands (or at the multiple wavelengths). As discussed previously, individual values or sets of values may be tagged or otherwise associated with information indicating a time when the emissions were detected. The digitized intensity values represent the temporal and spectral properties of the detected emissions in the multiple bands (or at the multiple wavelengths).

In block 1108, a determination is made whether the temporal and/or spectral characteristics of the emissions fall within appropriate authenticating parameter ranges (e.g., emission intensity ranges for multiple bands or wavelengths, an emission ratio range, and/or a decay time constant range). For example, as discussed previously, appropriate authenticating parameter ranges may be maintained by the authentication system in one or more tables or values that define the detection parameter space.

In conjunction with the spectral analysis, when a digitized intensity value falls within an appropriate emission intensity range for the time associated with the value (i.e., a time from discontinuation of the excitation energy when the intensity value was generated), a determination may be made that an emission having characteristics of emissions from one of multiple emitting ions (e.g., one of first and/or second emitting ions 110, 112, FIG. 1) has been detected. Otherwise, when a digitized intensity value falls outside the appropriate emission intensity range for the time associated with the value, a determination may be made that an emission having characteristics of emissions from one of multiple emitting ions has not been detected. According to an embodiment, multiple digitized intensity values may be analyzed, and the determination may allow one or more of the intensity values to fall outside the appropriate emission intensity range, while still yielding a positive result. In other words, the determination may be made to within an acceptable degree of accuracy. When a determination is made that emissions having characteristics of emissions from each of the multiple emitting ions have not been detected (i.e., the analysis indicates that the intensity values do not fall within the detection parameter space to within an acceptable degree of accuracy), the system may identify the article as being unauthentic.

In conjunction with a temporal analysis, the system may determine the decay times of emissions within the multiple bands or at the multiple wavelengths. Accordingly, appropriate authenticating parameter ranges also may include decay time constant ranges, decay half-lives, and so on. In an embodiment, the decay time(s) may be determined based on the detected intensities of the emissions at multiple times (e.g., t=0, t=0.1 millisecond, and so on). As discussed previously, upon removal of the excitation energy, the intensity of the emission decays over time, and the rate of decay for an emitting ion can be characterized by the decay time constant, a decay half-live, or other decay related parameters. According to an embodiment, the system determines whether or not the decay times of the emissions within the multiple bands (or at the multiple wavelengths) fall within the appropriate decay time constant ranges.

When the determination in block 1108 yields a positive result, then in block 1110, the system may identify the article as being authentic, and may take a corresponding action. For example, the system may produce a user-perceptible indication of authenticity, and/or may cause a routing component of the system to route the article toward a route or bin assigned for authentic articles. Alternatively, the determination in block 1108 yields a negative result, the system may identify the article as being unauthentic, and may take a corresponding action, in block 1112. For example, the system may produce a user-perceptible indication of unauthenticity, and/or may cause a routing component of the system to route the article toward a route or bin assigned for unauthentic articles.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A luminescent material comprising:
    first particles of a first inorganic host lattice having at least one first substance dispersed within the first inorganic host lattice, wherein the first particles are capable of producing first emissions having one or more first emission peaks at one or more first wavelengths, wherein the one or more first wavelengths include at least one first visible wavelength within the visible spectrum, and the first emissions at the first visible wavelength have a first decay half-life that is long enough for the first emissions at the first visible wavelength to be perceptible to the human eye for a first time period that begins when appropriate excitation of the luminescent material is discontinued; and
    second particles of a second inorganic host lattice having at least one second substance dispersed within the second inorganic host lattice, wherein the second particles are capable of producing second emissions having one or more second emission peaks at one or more second wavelengths, wherein the one or more second wavelengths include at least one second visible wavelength within the visible spectrum, wherein the second visible wavelength is different from the first visible wavelength, and the second emissions at the second visible wavelength have a second decay half-life that is longer than the first decay half-life by a decay time difference that is sufficient for the second emissions at the second visible wavelength to be perceptible to the human eye for a second time period that begins after the first time period;
    wherein the first inorganic host lattice and the second inorganic host lattice are selected from a group consisting of a fluoride, a halide, a borate, a gallate, a phosphate, a vanadate, an oxyhalide, a molybdate, a tungstate, a garnet, a germanate, a chlorophosphate, a niobate, a silicate, and mixtures thereof; and
    one or more media within which the first particles and the second particles are incorporated, wherein the one or more media are selected from a group consisting of an ink, an ink additive, a liquid, a gel, a ceramic, a metal, a textile, wood, fiber, paper pulp, paper, and mixtures thereof.

2. The luminescent material of claim 1, wherein the first visible wavelength corresponds to a first color, and the second visible wavelength corresponds to a second color that is different from the first color, and wherein the first color and the second color are different colors selected from a group consisting of red, orange, yellow, green, blue, and violet.

3. The luminescent material of claim 1, wherein the first visible wavelength and the second visible wavelength are different by at least 2 nanometers.

4. The luminescent material of claim 1, wherein the first inorganic host lattice and the second inorganic host lattice are selected from a group consisting of $Y_3Al_5O_{12}$ (YAG), $Gd_3Ga_5O_{12}$, $Y_3Ga_5O_{12}$ (YGG), $Y_3Fe_5O_{12}$ (YIG), YIG:YGG, $Zn_2SiO_4$, $Me_3MgSi_2O_8$ where Me is an alkaline earth element, and mixtures thereof.

5. The luminescent material of claim 1, wherein the first inorganic host lattice and the second inorganic host lattice are the same.

6. The luminescent material of claim 1, wherein the first inorganic host lattice and the second inorganic host lattice are different.

7. The luminescent material of claim 1, further comprising:
    one or more additional particles of one or more additional inorganic host lattices having one or more additional substances dispersed within the one or more additional inorganic host lattices, wherein the one or more additional particles are capable of producing one or more additional emissions having one or more additional emission peaks at one or more additional wavelengths, wherein the one or more additional wavelengths includes one or more additional visible wavelengths within the visible spectrum, wherein the one or more additional visible wavelengths are different from the first visible wavelength and the second visible wavelength, and the additional emissions at the one or more additional visible wavelengths have one or more additional decay half-lives that are different from the first decay half-life and the second decay half-life by one or more decay time differences that are sufficient for the additional emissions at the one or more additional visible wavelengths to be perceptible to the human eye for one or more additional time periods that begin after the first time period and the second time period.

8. The luminescent material of claim 1, wherein the first decay half-life is in a range of about 10 millisecond to about 100 milliseconds, and the second decay half-life is at least about 50 milliseconds.

9. The luminescent material of claim 1, wherein the second decay half-life is at least 10 milliseconds longer than the first decay half-life.

10. The luminescent material of claim 1, wherein the at least one first substance and the at least one second substance each include ions or atoms of elements selected from a group consisting of aluminum, chromium, manganese, iron, copper, silver, tin, antimony, cerium, praseodymium, neodymium, samarium, europium, gadolinium, terbium, dysprosium, holmium, erbium, thulium, ytterbium, lead, and mixtures thereof.

11. An article comprising:
first particles of a first inorganic host lattice having at least one first substance dispersed within the first inorganic host lattice, wherein the first particles are capable of producing first emissions having one or more first emission peaks at one or more first wavelengths, wherein the one or more first wavelengths includes at least one first visible wavelength within the visible spectrum, and the first emissions at the first visible wavelength have a first decay half-life that is long enough for the first emissions at the first visible wavelength to be perceptible to the human eye for a first time period that begins when appropriate excitation of the luminescent material is discontinued; and
second particles of a second inorganic host lattice having at least one second substance dispersed within the second inorganic host lattice, wherein the second particles are capable of producing second emissions having one or more second emission peaks at one or more second wavelengths, wherein the one or more second wavelengths includes at least one second visible wavelength within the visible spectrum, wherein the second visible wavelength is different from the first visible wavelength, and the second emissions at the second visible wavelength have a second decay half-life that is longer than the first decay half-life by a decay time difference that is sufficient for the second emissions at the second visible wavelength to be perceptible to the human eye for a second time period that begins after the first time period,
wherein the first inorganic host lattice and the second inorganic host lattice are selected from a group consisting of a fluoride, a halide, a borate, a gallate, a phosphate, a vanadate, an oxyhalide, a molybdate, a tungstate, a garnet, a germanate, a chlorophosphate, a niobate, a silicate, and mixtures thereof; and
one or more media within which the first particles and the second particles are incorporated, wherein the one or more media are selected from a group consisting of an ink, an ink additive, a liquid, a gel, a ceramic, a metal, a textile, wood, fiber, paper pulp, paper, and mixtures thereof;
wherein the article is an article selected from a group consisting of an identification card, a driver's license, a passport, identity papers, a banknote, a check, a document, a paper, a stock certificate, a packaging component, a credit card, a bank card, a label, a seal, a postage stamp, a token, a liquid, an animal, and a biological sample.

12. The article of claim 11, further comprising:
one or more additional particles of one or more additional inorganic host lattices having one or more additional substances dispersed within the one or more additional inorganic host lattices, wherein the one or more additional particles are capable of producing one or more additional emissions having one or more additional emission peaks at one or more additional wavelengths, wherein the one or more additional wavelengths includes one or more additional visible wavelengths within the visible spectrum, wherein the one or more additional visible wavelengths are different from the first visible wavelength and the second visible wavelength, and the additional emissions at the one or more additional visible wavelengths have one or more additional decay half-lives that are different from the first decay half-life and the second decay half-life by one or more decay time differences that are sufficient for the additional emissions at the one or more additional visible wavelengths to be perceptible to the human eye for one or more additional time periods that begin after the first time period.

13. The article of claim 11, further comprising:
a substrate; and
one or more features, wherein the one or more features comprise the one or more media within which the first particles and the second particles are included.

14. The article of claim 11, wherein the one or more media comprises:
a first medium, wherein the first particles are included in the first medium; and
a second medium, wherein the second substance are included in the second medium.

15. The article of claim 11, wherein the article includes multiple, spatially distinct regions, and wherein a first region of the multiple regions includes a first ratio of the first particles to the second particles, and a second region of the multiple regions includes a second ratio of the first particles to the second particles, wherein the first ratio and the second ratio are different.

16. The article of claim 11, further comprising:
a substrate that comprises the one or more media within which the first particles and the second particles are included.

17. The article of claim 11, further comprising:
a substrate that comprises one or more media, wherein the first particles are included in the substrate; and
a feature that comprises the one or more media, wherein the feature is applied to or embedded within the substrate, wherein the second particles are included in the feature.

* * * * *